United States Patent [19]

Oswald et al.

[11] 4,075,332
[45] Feb. 21, 1978

[54] PESTICIDAL O,S'-DIALKYL S-HYDROCARBYLTHIOALKYL DITHIOPHOSPHATES AND OXIDIZED DERIVATIVES THEREOF

[75] Inventors: Alexis A. Oswald, Mountainside; Paul L. Valint, Jr., Woodbridge, both of N.J.

[73] Assignee: Exxon Research & Engineering Co., Linden, N.J.

[21] Appl. No.: 677,719

[22] Filed: Apr. 16, 1976

Related U.S. Application Data

[63] Continuation of Ser. No. 505,109, July 11, 1974, abandoned, which is a continuation-in-part of Ser. No. 210,229, Dec. 20, 1971, abandoned, which is a continuation-in-part of Ser. No. 173,267, Aug. 19, 1971, abandoned, which is a continuation of Ser. No. 821,117, May 1, 1969, abandoned.

[51] Int. Cl.$^2$ .............................................. A01N 9/36
[52] U.S. Cl. .............................. 424/216; 424/DIG. 8; 71/87; 260/948
[58] Field of Search .................. 424/215, 216, DIG. 8

[56] References Cited

U.S. PATENT DOCUMENTS

| | | | |
|---|---|---|---|
| 2,881,201 | 4/1959 | Schrader | 260/461 |
| 3,078,295 | 2/1963 | Schrader | 260/461 |
| 3,660,543 | 5/1972 | Mueller et al. | 260/948 |

*Primary Examiner*—V. D. Turner
*Attorney, Agent, or Firm*—Robert J. Baran; Albert P. Halluin

[57] ABSTRACT

Dithiophosphates of the general formula:

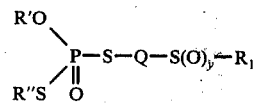

wherein R' is methyl or ethyl; R" is primary or secondary $C_3$–$C_4$ alkyl; Q is a $C_1$–$C_4$ alkylene; $y$ is 0–2; $R_1$ is $C_1$–$C_4$ alkyl and aryl are novel compounds having excellent pesticidal properties against insects, mites and nematodes. O-Ethyl S'-n-propyl S-alkylthioalkyl dithiohosphates in which each alkyl group has from 1 to 3 carbon atoms, are especially outstanding as pesticides of reduced mammalian toxicity and are useful in the control of the highly pesticide resistant insects of the Order of Lepidoptera.

28 Claims, No Drawings

PESTICIDAL O,S'-DIALKYL S-HYDROCARBYLTHIOALKYL DITHIOPHOSPHATES AND OXIDIZED DERIVATIVES THEREOF

CROSS-REFERENCE TO RELATED APPLICATIONS

This application is a continuation of application Ser. No. 505,109, filed July 11, 1974, now abandoned, which in turn is a continuation-in-part of application Ser. No. 210,229, filed Dec. 20, 1971, now abandoned, which in turn is a continuation-in-part of application Ser. No. 173,267, filed Aug. 9, 1971, now abandoned. Application Ser. No. 173,267 is a continuation of application Ser. No. 821,117, filed May 1, 1969, now abandoned.

SUMMARY OF THE INVENTION

This invention relates to new O,S-dialkyl S-hydrocarbylthioalkyl dithiophosphates and their oxidized derivatives. In one aspect, this invention relates to novel, insecticidal uses of these dithiophosphates. Most specifically, this invention relates to the use of O-ethyl S'-n-propyl S-hydrocarbylthioalkyl dithiophosphates for controlling the insects of the Order of Lepidoptera.

PRIOR ART

Dialkyl dithiophosphate esters of formula $(R'O)_2PS_2R$ represent a very important class of insecticides. O,O'Dialkyl dithiophosphate esters were especially widely studied. Most of the commercially important dithiophosphate esters are of this class. Their synthesis and pesticidal action is described by Gerhard Schrader in his monograph, entitled "Die Entwicklung Neuer Insektizider Phosphorsäure-Ester", which was published by Verlag Chemie GmbH., in Weinheim, W. Germany, in 1963. On pages 338–427 of this monograph, several commercially important O,O'-dialkyl S-hydrocarbylthioalkyl dithiophosphates, $(R'O)_2PS_2C_nH_{2n}SR_1$, are discussed.

The search is being continued to find novel dithiophosphates of superior pesticidal effectiveness and reduced mammalian toxicity. One of the areas of present research interest is in the field of O,S'-dialkyl dithiophosphate esters of formula

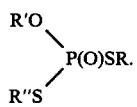

Researchers of the Sumitomo Chemical Company, Ltd., of Osaka, Japan, published in Dutch Pat. No. 67/17383 that O,S'-dialkyl dithiophosphate esters are in general good insecticides with a surprising fungicidal action. The patent discloses the synthesis and biological testing of 108 compounds of widely varying formula. However, it does not describe any structure activity correlations. Another Sumitomo publication, South African Patent Application No. 68-3116, claims that phenyl esters of O,S'-dialkyl dithiophosphoric acids are particularly attractive pesticides.

The pesticidal activity of hydrocarbylthioalkyl esters of O,S'-dialkyl dithiophosphoric acids was first studied by Gerhard Schrader. In German Pat. No. 1,032,247, he describes the synthesis of the ethylthioethyl ester of O,S'-diethyl dithiophosphoric acid:

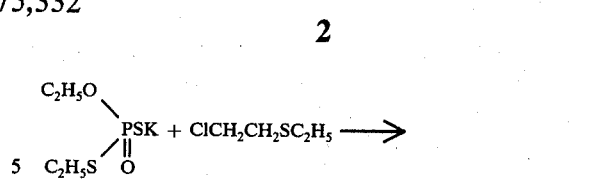

In German Pat. No. 1,136,328, Schrader also described the synthesis of an unsymmetrically substituted O,S'-dialkyl dithiophosphate, i.e.

A comparison of the insecticidal activity of this unsymmetrical compound with those of the corresponding O,S'-dimethyl and O,S'-diethyl dithiophosphates in the above patent showed that both symmetrically substituted compounds had activities superior to the unsymmetrical compound.

For the synthesis of O,S'-dialkyl S-hydrocarbylthioalkyl dithiophosphates from the corresponding O,S'-dialkyl dithiophosphate salts Schrader was issued U.S. Pat. No. 3,078,295. This patent describes a number of O,S'-dimethyl and O,S'-diethyl dithiophosphate esters.

In British Pat. No. 806,148, Schrader claims O,S'-dialkyl hydrocarbylthioalkyl dithiophosphates broadly, without indicating that the unsymmetricaly substituted O,S'-dialkyl dithiophosphates are of interest.

In view of the extensive pioneering work of Schrader and large current effort of Sumitomo, it was completely unexpected that unsymmetrical compounds of a specific well-defined type of structure falling within their broad generic disclosure would show generally superior pesticidal properties. More specifically, the compounds of the present invention were surprisingly found to have a unique combination of broad pesticidal spectrum, high activity against pesticide resistant insects of the Order of Lepidoptera and reduced mammalian toxicity.

DETAILED DISCLOSURE

In the present invention, new types of dialkyl dithiophosphate esters, i.e., novel O,S'-dialkyl S-hydrocarbylthioalkyl dithiophosphates, are disclosed. It is also disclosed herein that the new unsymmetrically substituted O,S'-dialkyl dithiophosphate esters are unusually active and safe pesticides, especially useful for the control of insects belonging to the Lepidoptera Order.

The new products claimed in the present invention are O-methyl and ethyl S'-propyl and butyl S-hydrocarbyl-thio alkyl dithiophosphates. The new compositions are represented by the following general formula:

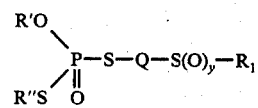

wherein R' is methyl and ethyl, preferably ethyl; R" is primary and secondary $C_3$–$C_4$ alkyl, preferably a primary $C_3$–$C_4$ alkyl, more preferably, n-propyl and isobutyl, most preferably n-propyl; $R_1$ is a $C_1$ to $C_{10}$ substituted or nonsubstituted hydrocarbyl group, preferably $C_1$ to $C_4$ substituted or nonsubstituted alkyl and $C_6$ to $C_{10}$ substituted or nonsubstituted aryl, containing such exemplary substituents as halogen, alkylthio, alkylsulfonyl, alkylcarbonyl, carboalkoxy, alkylamido, cyano, alkyl, nitro, phenyl, more preferably $R_1$ is $C_1$ to $C_4$ alkyl, substituted and unsubstituted $C_6$ to $C_8$ phenyl, most preferably, $R_1$ is $C_1$ to $C_3$ alkyl, phenyl, 4-chlorophenyl; Q is a $C_1$ to $C_4$ alkylene, preferably a $C_1$ to $C_3$ alkylene, more preferably, methylene, dimethylene, trimethylene and propylene radical, most preferably, propylene; $y$ is 0 to 2, preferably 0 to 1, most preferably 0.

The preferred compositions of the present invention include compounds of the following general structures:

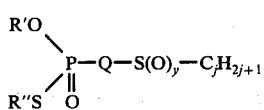
(a)

wherein R', R", Q and $y$ are the same as stated hereinabove and $j$ is 1 to 4, preferably 1 to 3, more preferably 1 to 2, most preferably 1, provided that when Q is methylene $y$ is 0.

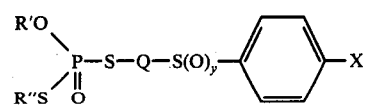
(b)

wherein R', R", Q, $y$ are as previously defined above; X is hydrogen, halogen, methylthio, methylsulfonyl, cyano, etc., preferably hydrogen and chlorine.

More specific compositions of the present composition include:

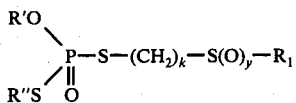
(c)

wherein R', R", $R_1$ and $y$ are as previously defined, $k$ is 1 to 4, preferably 1 to 3, more preferably 2 to 3, most preferably 2 provided that, when $k$ is 1, $y$ is 0.

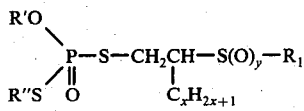
(d)

wherein the meaning of R', R", $R_1$ and $y$ as previously defined and $x$ is 1 to 2, preferably 1.

Most specifically, compositions of the present invention include those having the general formula:

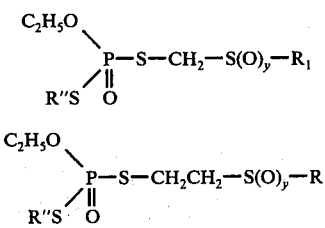
(e)
(f)

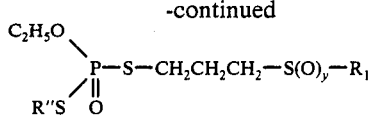
(g)

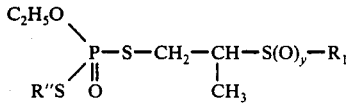
(h)

wherein the meaning of R", $R_1$ and $y$ is the same as before.

Specific O-ethyl S'-n-propyl dithiophosphate compositions of the present invention are shown by the following generic formula:

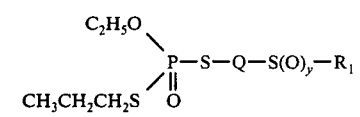
(i)

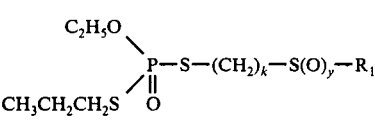
(j)

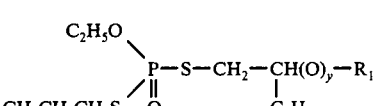
(k)

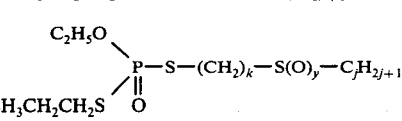
(l)

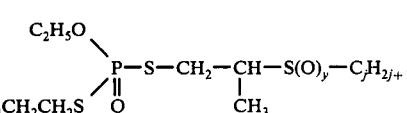
(m)

wherein the meaning of symbols is as it was previously defined.

Examples of $R_1$ are: methyl, ethyl, n-propyl, isopropyl, n-butyl, isobutyl, sec.butyl, acetyl, chloropropyl, bromoethyl, fluoromethyl, methylthiomethyl, methylsulfonylphenyl, xylyl, carboethoxymethyl, cyanoethyl, nitrotolyl, trifluoromethylphenyl, dichlorophenyl.

Non-limiting examples of the S-hydrocarbylthioalkyl O,S'-dialkyl dithiophosphate compositions include, e.g.: S-methylthiomethyl O-methyl S'-n-propyl dithiophosphate, S-chlorophenylthiomethyl O-ethyl S'-butyl dithiophosphates, S-n-propylthiomethyl O-ethyl S'-isobutyl dithiophosphate, S-n-hexadecylthioethyl O-ethyl S'-sec.butyl dithiophosphate, S-(2-ethylthiobutyl) O-ethyl S'-n-propyl dithiophosphate, S-(3-methylthiopropyl O-ethyl S'-n-propyl dithiophosphate, S-(2-methylthiobutyl) O-ethyl S'-n-propyl dithiophosphate, S-xylylthiomethyl O-ethyl S'-n-butyl dithiophosphates, S-(3-sec.butylthiopropyl O-ethyl S'-n-propyl dithiophosphate) s-trichlorophenylthiomethyl O-ethyl S'-n-propyl dithiophosphates, S-bis(methylthiopropyl) O-ethyl S'-n-propyl dithiophosphate, S-methylsulfonylphenylthiomethyl O-ethyl S'-n-propyl dithiophosphates, S-(2-ethylsulfonylethyl) O-ethyl S'-n-propyl dithiophosphate, S-(2-ethylsulfonylpropyl) O-ethyl S'-sec.butyl dithiophosphate, S-(3-ethylsulfonylbutyl) O-ethyl S'-n-propyl dithiophosphate, S-chlorophenylsulfonylmethyl O-ethyl S'-n-propyl dithiophosphates, S-

(2-ethylsulfinylpropyl) O-ethyl S'-n-propyl dithiophosphate, and S-(3-methylsulfinylpropyl) O-ethyl S'-n-propyl dithiophosphate.

The new pesticidal O,S'-dialkyl S-hydrocarbylthioalkyl dithiophosphates are prepared from dithiophosphate esters selected from the group consisting of S-hydrocarbylthioalkyl and S-alkenyl esters of O,O'-dialkyl dithiophosphoric acids. The processes comprise a combination of dealkylation and alkylation reactions, both in the liquid phase. Most generally, this combination of reactions can be schematically represented in the following manner:

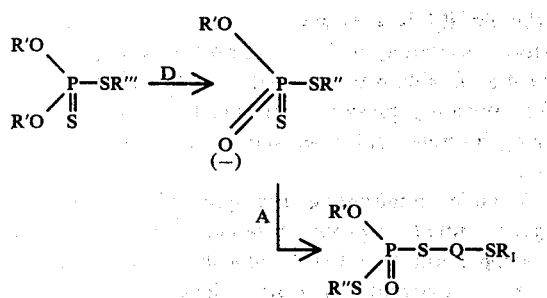

wherein R', R", Q and $R_1$ are defined above; R" is a hydrocarbylthioalkyl radical or an alkyl group having olefinic unsaturation; D is a dealkylating agent, preferably a nitrogen or phosphorus base or a thiolate or inorganic salt; A is an alkylation agent preferably an alkyl halide, alkyl sulfonate, dialkyl sulfate, alkyl phosphate, trialkyl phosphite or the combination of such an alkylating agent with another alkylating agent such as a thiol.

If R'" is a hydrocarbylthioalkyl radical, only one alkylating agent is used according to the following scheme:

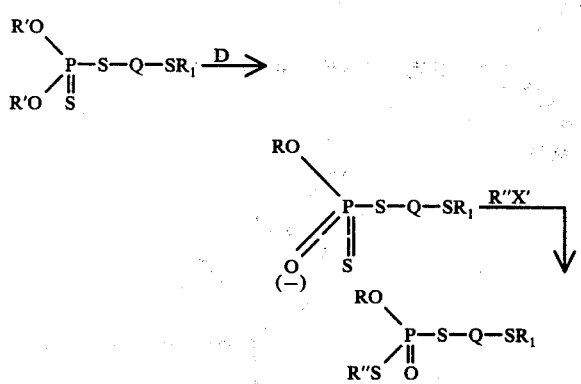

wherein all the symbols are as previously defined and the additional R"X' symbol represent an alkylating agent such as an alkyl halide, alkyl sulfonate, alkyl phosphate, etc.

If R'" is an alkyl group having olefinic unsaturation, a combination of two types of alkylating agents is used according to the following scheme:

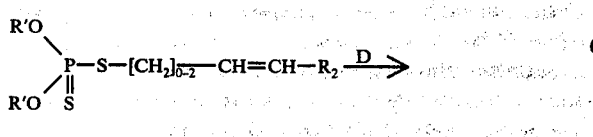

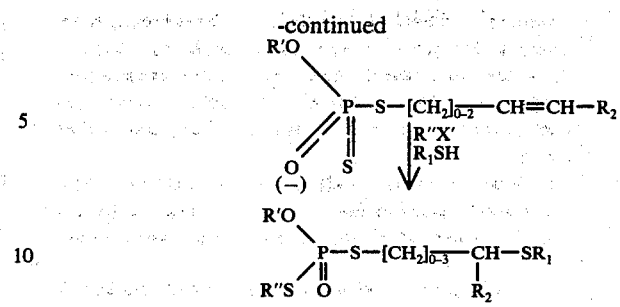

wherein all the symbols are as previously defined, $R_1SH$ representing an aliphatic or aromatic thiol, and $R_2$ being a hydrogen or alkyl group.

Where the dithiophosphate ester reactant has the general formula:

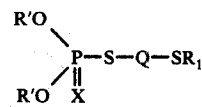

non-limiting examples of suitable reactants include diethyl methylthiomethyl dithiophosphate, dimethyl phenylthiomethyl dithiophosphate, diethyl chlorophenylthiomethyl dithiophosphates, diethyl ethylthioethyl dithiophsophate, diethyl 2-methylthiopropyl dithiophosphate, dimethyl 2-methylthiopropyl dithiophosphate, diethyl 2-n-propylthiobutyl dithiophosphate, dimethyl 2-isopropylthiobutyl dithiophosphate, etc.

Where the dithiophosphate ester reactant has the general formula:

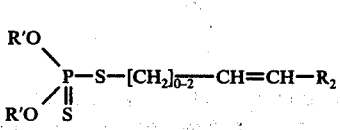

$R_2$ is hydrogen or a $C_1$ to $C_{16}$ alkyl radical, the alkyl radical preferably being in the $C_1$ to $C_3$ range. Nonlimiting examples of suitable O,O'-dialkyl S-alkenyl dithiophosphate reactants include dimethyl propenyl dithiophosphate, diethyl butenyl dithiophosphate, diethyl hexenyl dithiophosphate, dimethyl butenyl dithiophosphate, methyl allyl dithiophosphate, etc.

The dealkylating agents for the O,O'-dialkyl dithiophosphate esters are preferably selected from the following groups:

| $(R_4)_3G$ | $R_5SM$ | XM |
|---|---|---|
| I | II | III | wherein $R_4$ is hydrogen, a $C_1$ to $C_8$ alkyl or monosubstituted alkyl, preferably hydrogen and $C_1$ to $C_4$ alkyl, most preferably methyl; G is a nitrogen or phosphorus base; $R_5$ is a $C_1$ to $C_8$ hydrocarbyl, preferably $C_1$ to $C_4$ alkyl; M is an alkali or alkaline earth metal, or tetraalkyl ammonium; X is chlorine, bromine or iodine.

Nonlimiting, suitable dealkylating reagents for the O,O'-dialkyl dithiophosphate esters are exemplified by the following compounds:

I. Ammonia, propylamine, diethylamine, trimethylamine, tetramethylethylenediamine, N-methyl pyrrolidine, hydroxyethylamine, benzyldimethylamine, triethylenediamine, trimethylphosphine, tributylphosphine, phosphine and other nitrogen and phosphorus bases.

II. Sodium methanethiolate, potassium ethanethiolate, potassium ethylxanthate, tetramethylammonium propanethiolate, sodium hydrogen sulfide, and other thiolate salts.

III. Lithium chloride, sodium iodide, calcium chloride, tetrabutylammonium iodide, tetrahexylphosphonium bromide, and similar metal and ammonium salts.

The dealkylation reaction of O,O'-dialkyl-S-hydrocarbylthioalkyl dithiophosphates by nitrogen and phosphorus bases is shown by the following scheme:

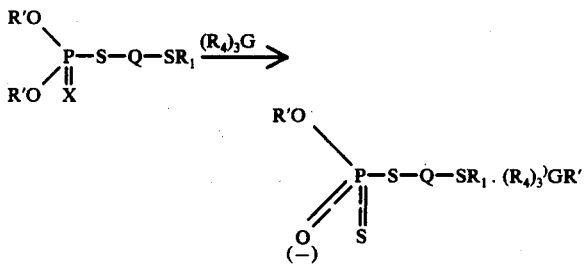

A similar dealkylation by thiolates is shown below:

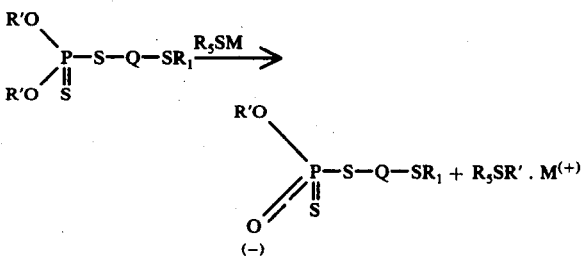

If the dealkylating reagent is a salt, a trialkyl amine or a trialkylphosphine, the resulting products of dealkylation are phosphate salts of ionic character. However, in the case of not completely substituted amines and phosphines, the product is partly hydrogen bonded:

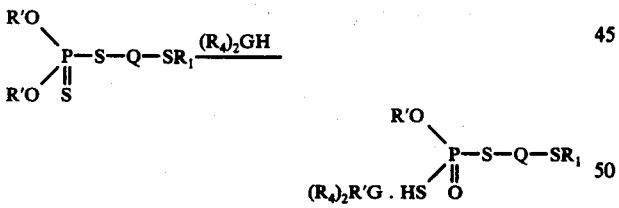

The reactions of olefinically unsaturated O,O'-dialkyl dithiophosphates, in general occur in the manner described in our U.S. Pat. No. 3,662,034, whose disclosure in this regard is incorporated herein by reference. Such reactions are a part of the present multistep process.

The dealkylation of alkylthioalkyl O,O'-dialkyl dithiophosphates also occurs selectively with the removal of an O-alkyl group. It is surprising to observe that the dealkylation of 2-alkylthioethyl O,O'-dialkyl dithiophosphates does not result in the removal of alkylthioethyl groups which are believed to be stabilized in the form of the corresponding episulfonium ions.

The alkylation of S-alkylthioalkyl O-alkyl dithiophosphate salts and complexes is also a highly selective process. It occurs exclusively on the sulfur atom to yield the corresponding S-alkylthioalkyl O,S'-dialkyl dithiophosphates. With metal salts, for example, the following reaction occurs.

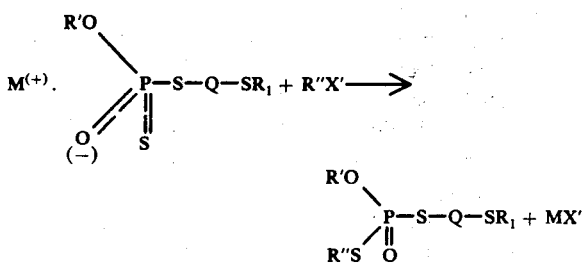

wherein R" is a primary or secondary $C_3$-$C_4$ alkyl group, preferably a $C_3$ to $C_4$ primary alkyl group, and most preferably n-propyl; and X' is the leaving group in the alkylating process, representative examples of X' being bromine, chlorine, iodine, phosphate, sulfonate, etc.

Suitable, nonlimiting examples of the alkylating agents include n-propyl bromide, n-propyl chloride, isopropyl iodide, n-butyl chloride, sec.butyl tosylate, n-propyl phosphite, isobutyl phosphate, tri-n-propyl phosphite, etc.

The net result of the dealkylation-alkylation processes from the viewpoint of the types of chemical structures involved is the isomerization of a thionothiolphosphate to a dithiolphosphate ester. In the case of the hydrocarbylthioalkyl dithiophosphates, these processes provide the final pesticidal compounds of this invention. Starting with unsaturated dithiophosphates, however, necessitates the use of an additional process step, i.e., the addition of a thiol to the unsaturated dithiolphosphate:

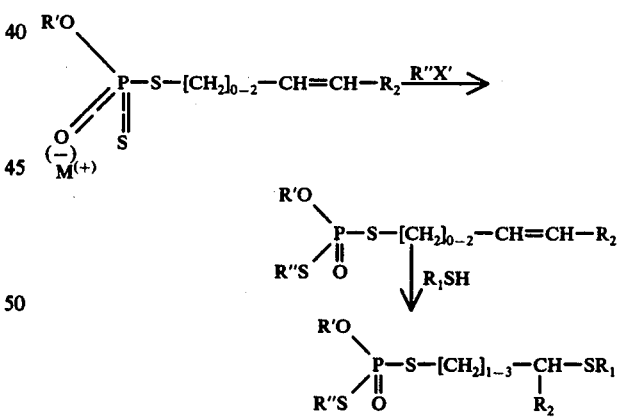

wherein all of the above symbols are as previously defined. Examples of useful thiols are: methanethiol, hexadecanethiol, propanethiol, octanethiol, benzenethiol, toluenethiol, chlorobenzenethiol trichlorobenzenethiol, cyclohexanethiol, methylsulfonylbenzenethiol, cyanobenzenethiol, etc.

The addition of thiols to the unsaturated dithiolphosphates can result in the attachment of the thiol sulfur at either of the olefinic carbons. In the case of terminally unsaturated dithiolphosphates, a free radical type thiol addition results in primary sulfide derivatives, i.e., addition occurs in an anti-Markovnikov manner:

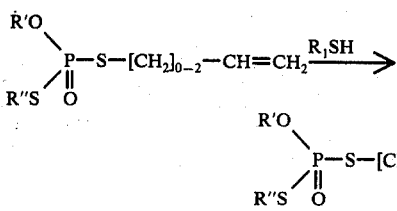

Radical type addition to vinylic dithiolphosphates, in general, occurs in a highly selective manner

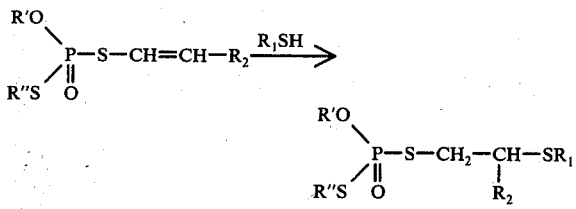

In contrast, radical addition to internally allylic compounds yields dithiolphosphate adducts having sulfur substitution mainly on the unsaturated carbon closer to the phosphorus; e.g.,

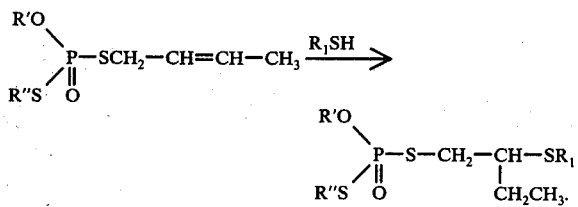

The various process conditions are set forth in our copending U.S. Pat. Application Ser. No. 377,872, Ser. No. 377,873 and Ser. No. 377,874, all filed on July 9, 1973, whose disclosures in this regard are incorporated herein by reference.

PESTICIDE COMPOSITIONS

While the compositions of the present invention are believed to be all novel pesticides with surprising properties, they possess different relative degrees of pesticidal activity. The toxicities of our pesticides are also different. For economical pesticidal uses certain novel compositions are preferred because they are effective at lower concentration and/or are safer to apply.

The unsymmetrical O,S'-dialkyl S-hydrocarbylthioalkyl dithiophosphate pesticides

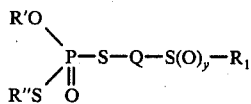

preferably have a molecular weight under 400. For a higher stability, coupled with reduced toxicity the O-alkyl, i.e., R' group, should be surprisingly ethyl rather than methyl. Also unexpectedly the S-alkyl group, i.e., R" group, should be a primary or secondary propyl or butyl group for high activity and reduced toxicity. More preferably, the R" group is n-propyl or isobutyl for high activity. Surprisingly, the highest activity is obtained when R" is n-propyl. Although all the novel compounds have a surprisingly high activity against the insects belonging to the Order of Lepidoptera, the S-n-propyl derivatives are particularly effective.

The hydrocarbylthioalkyl esterifying groups, i.e., $-Q-S(O)_y-R_1$ are known for O,O'-dialkyl dithiophosphates. For the O,S'-dialkyl dithiophosphates of the present invention, it is particularly advantageous if Q is a $C_1$ to $C_3$ alkylene, most preferably propylene and $R_1$ is a $C_1$ to $C_4$ alkyl, $C_6$ to $C_8$ substituted and unsubstituted phenyl, most preferably $C_1$ to $C_3$ alkyl, phenyl, 4-chlorophenyl. For systemic activity, $R_1$ should be a $C_1$ to $C_3$ alkyl, preferably a methyl group.

The number $y$ is preferably 0, i.e., the compounds preferably contain a non-oxidized thioether group. However, $y$ can be 1 or 2; i.e., oxidized compounds having a sulfoxide or sulfone group are included provided that Q is $C_2$ to $C_4$.

While many of the preferred pesticidal dithiophosphates of the present invention have the well known lower O-alkoxy and S-hydrocarbylthioalkyl esterifying groups, their higher S'-alkyl group is believed to be novel. Most specifically, these unsymmetrical compositions exhibit the presence of S-n-propyl or S-isobutyl groups. Unexpectedly, these groups are critical in contributing very desirable, superior pesticidal properties to have pesticidal compositions, whereas similar known unsymmetrical, O,S'-dialkyl esters having S-methyl or S-ethyl groups, show an insecticidal activity markedly inferior to that of the corresponding symmetrical esters. The surprising result of the present combination of substituents is a new type of pesticide having a broad spectrum of activity. Among the desirable pesticidal properties of the new compositions, their activity against insects of the Order of Lepidoptera is particularly outstanding. This order of insects is usually difficult to control. For example, the Southern army worm shows a high resistance against most of the known pest control chemicals. Our compositions, however, show an unusual activity against the Southern army worm.

It is similarly unexpected and important that the novel compositions have low toxicities against warm blooded animals and are therefore safe to use. The appearance of the low toxicity is again specifically associated with the presence of the S-n-propyl or S-primary isobutyl groups in these molecules. These groups counteract the effect of the usually highly toxic O-ethyl group. This low toxicity coupled with high pesticidal activity, i.e., high therapeutical index, is essential for animal health applications.

The broad insecticidal activity of the present compositions is shown by the many insects controlled. For example, the following insects of the Lepidoptera Order have responded to treatment: boll worm and cabbage looper of the Family Noctuidae; salt marsh caterpillar of F. Arctiidae; artichoke plum moth of F. Pterophoridae, leaf roller of F. Tortricidae. The new compositions were found effective against the following further examples of insects: boll weevil, beet armyworm, budworm, Colorado potato beetle, confused flour beetle, corn ear worms, corn silk fly, cucumber beetles, cutworm, European corn borer, diamond black month, leafhopper, lygus bug, grasshopper, pea aphid, salt marsh caterpillar, potato tuberworm, spider beetle, thrips, stinkbugs, potato flea beetles, mosquito larvae, louse. Furthermore, compositions have repellent action, for example, towards the confused flour beetle. Beyond insects, the new pesticides control mites, nematodes and some fungi. Some of the new pesticides have a herbicidal action. Others of low mammalian toxicity were found to be promising for animal health control.

PESTICIDAL FORMULATIONS

As previously noted, the esters of this invention are useful as pesticides, particularly as insecticides. When used as insecticides, they are preferably formulated with a suitable carrier or diluent or combinations thereof.

The term "carrier" or "diluent" as used herein means a material which can be inorganic or organic and synthetic or of natural origin, with which the active ingredient or ingredients of this invention can be mixed to facilitate its storage, transportation and handling, and application to the insects to be treated. The carrier is preferably biologically and chemically inert, and, as used, can be a solid or a fluid. When solid carriers are used, they are preferably particulate, granular, or pelleted; however, other shapes and sizes of solid carriers can be employed as well. Such preferably solid carriers can be naturally occurring materials; although subsequently subjected to grinding, sieving, purification, and/or other treatments — including for example, gypsum, tripolyte; diatomaceous earth; mineral silicates, such as mica, vermiculite, talc, and pyrophyllite; clays of the montmorillonite, kaolinite, or attapulgite groups; or calcite and dolomite; etc. Carriers produced synthetically, as for example, synthetic hydrated silica oxides and synthetic calcium silicates can also be used, and many proprietary products of this type are available commercially. The carrier can also be an elemental substance such as sulfur or carbon, preferably an activated carbon. If the carrier possesses intrinsic catalytic activity such that it would decompose the active ingredient, it is advantageous to incorporate a stabilizing agent, as for example, polyglycols such as diethylene glycol to neutralize this activity and thereby prevent possible decomposition of the active ingredient.

For some purposes, a resinous or waxy carrier can be used, preferably one which is solvent-soluble or thermoplastic, including fusible. Examples of such carriers are natural or synthetic resins such as a coumarin resin; rosin; copal; shellac; dammar; polyvinyl chloride; styrene polymers and copolymers; a solid grade of polychlorophenol such as is available under the registered trademark "Arochlor"; a bitumen; an asphaltite; a wax, for example beeswax or a mineral wax such as paraffin wax or Montan wax, or a chlorinated mineral wax or a microcrystalline wax such as those available under the registered trademark "Mikrovan Wax". Compositions comprising said resinous or waxy carriers are preferably in a granular of pelleted form.

Fluid carriers can be liquids, as for example, water, or an organic fluid, including liquefied, normally gaseous materials, and can be solvents or nonsolvents for the active material. For example, the horticultural petroleum spray oils boiling in the range of from about 275° to about 575° F., or boiling in the range of from about 575° to about 1000° F., and having an unsulfonatable residue of at least about 75% and preferably of at least about 90%, or mixtures of these two types of oils are particularly suitable liquid carriers.

The carrier can be mixed or formulated with the active material during its manufacture or at any stage subsequently. The carrier can be mixed or formulated with the active material in any proportion depending upon the nature of the carrier. One or more carriers, moreover, can be used in combination.

The compositions of this invention can be concentrated, suitable for storage and transport, and contain for example, from about 5 to about 95% by weight of the active ingredient, preferably from about 20 to about 80% by weight. These concentrates can be diluted with the same or a different carrier to a concentration suitable for application. The compositions of this invention can also be dilute compositions suitable for application in a manner well known in the art. In general, concentrations of about 0.1 to about 10% by weight of the active material, based upon the total weight of the composition, are satisfactory, although lower and higher concentrations can be applied if necessary.

The compositions of this invention can also be formulated as dusts. These comprise an admixture of the active ingredient and a finely powdered solid carrier such as aforedescribed. The powdered carriers can be oil-treated to improve adhesion to the surface to which they are applied. These dusts can be concentrates, in which case a highly sorptive carrier is preferably used. These require dilution with the same or different finely powdered carriers, which can be of lower sorptive capacity to a concentration suitable for application.

The compositions of this invention can also be formulated as wettable powders comprising a major proportion of the active ingredient mixed with a dispersant, i.e., a deflocculating or suspending agent, and if desired, a finely divided solid carrier and/or a wetting agent. The active ingredient can be in particulate form or adsorbed on the carrier, and preferably constitutes at least about 10%, more preferably at least about 35%, by weight, of the final pesticidal composition. The concentration of the dispersing agent should in general be between about 0.5 and about 5% by weight of the total composition, although larger or smaller amounts can be used if desired.

The dispersant or dispersing agent used in the compositions or formulations of this invention can be any substance having definite dispersant, i.e., deflocculating or suspending properties as distinct from wetting properties, although the substances can also possess wetting properties as well.

The dispersant or dispersing agent used can be a protective colloid such as gelatin, glue, casein, gums, or a synthetic polymeric material such as polyvinyl alcohol and methyl cellulose, etc. Preferably, however, the dispersants or dispersing agents used are sodium or calcium salts of high molecular weight sulfonic acids, as for example, the sodium or calcium salts of lignin sulfonic acids derived from sulfite cellulose waste liquors. The calcium or sodium salts of condensed aromatic sulfonic acids, for example, the products known as "Tamol 731", are also suitable.

The wetting agents used can be nonionic type surfactants, as for example, the condensation products of fatty acids, containing at least 12, preferably 16 to 20, carbon atoms in the molecule of abietic acid or naphthenic acid obtained in the refining of petroleum oil fractions, with alkylene oxides such as ethylene oxides or propylene oxides, or with both ethylene oxide and propylene oxide, as for example, the condensation products of oleic acid and ethylene oxide containing about 6 to 15 ethylene oxide units in the molecule. Other nonionic wetting agents like polyalkylene oxide polymers, commercially known as "Pluronics" can be used. Partial esters of the above acids with polyhydric alcohols such as glycerol, polyglycerol, sorbitol or mannitol, etc. can also be used.

Suitable anionic wetting agents include the alkali metal salts, preferably sodium salts, of sulfuric acid or sulphonic acids containing at least 10 carbon atoms in a molecule; for example, the sodium secondary alkyl sulfates, dialkylsodium sulfosuccinates available under the registered trademark "Teepol", sodium sulfonates, castor oil, sodium dodecylbenzene sulfonate, etc.

Granulated or pelleted compositions comprising a suitable carrier having the active ingredients incorporated therein are also included in this invention. These can be prepared by impregnating a granular carrier with a solution of an active ingredient or by granulating a mixture of a finely divided carrier and the active ingredients. The carrier used can contain a fertilizer or a fertilizer mixture, such as for example, a superphosphate.

The compositions of this invention can be formulated also as solutions of the active ingredients and an organic solvent or mixtures of solvent, such as for example, alcohols, ketones, especially acetone, ethers, hydrocarbons, etc. When the toxicant itself is a liquid, it can be sprayed upon the insects or fungi without further dilution.

Petroleum hydrocarbon fractions used as solvents should preferably have a flash point of about 73° F., an example of this being a refined aromatic extract of kerosene. Auxiliary solvents such as alcohols, ketones, and polyalkylene glycol ethers and esters can be used in conjunction with these petroleum solvents.

Compositions of the present invention can also be formulated as emulsifiable concentrates which are concentrated solutions or dispersions of the active ingredients in an organic liquid, preferably a water-insoluble organic liquid containing an added emulsifying agent. These concentrates can also contain a proportion of water, for example, 50% by volume, based upon the total composition to facilitate subsequent dilution with water. Suitable organic liquids include, e.g., the above petroleum hydrocarbon fractions previously described.

The emulsifying agents or emulsifiers are generally of the type producing water-in-oil type emulsions which are suitable for application by low volume spraying, or they can be emulsifiers of the type producing oil-in-water emulsions producing concentrates which can be diluted with relatively large volumes of water for application by high volume spraying or relatively small volumes of water for low volume spraying. In such emulsions, the active ingredient is preferably in a nonaqueous phase.

The present invention is further illustrated in greater detail by the following examples, but it is to be understood that the present invention, in its broadest aspects, is not necessarily limited in terms of the reactants or specific temperatures, residence times, separation techniques, and other process conditions, etc.; or dosage levels, exposure times, insects used, etc. by which the compounds and/or formulations described and claimed are prepared and/or used.

EXAMPLES

Synthesis of S-Hydrocarbylthioalkyl O,S'-Dialkyl Dithiophosphates and Oxidized Derivatives

Example 1 — O-Ethyl S-1-Propyl S'-2-Methylthioethyl Dithiophosphate

A solution of 313.6g(5.6 moles) of potassium hydroxide in 5 liters of absolute ethanol was saturated with hydrogen sulfide at 0° C. O,O-diethyl-S-n-propyl dithiophosphate (1276.8 g., 5.6 moles) was added and the mixture was kept at ambient temperature for 12 hours then heated to reflux for 5 hours. The resultant solution was concentrated under vacuum to give a white solid residue which was washed with ether. The solid was separated by filtration to yield 876 g. (66%) of potassium O-ethyl S-1-propyl dithiophosphate as shown by its nmr spectrum.

To a solution of 35.7 g. (0.15 mole) of potassium O-ethyl S-1-propyl dithiophosphate in 500 ml. of acetonitrile, 16.6 g (0.15 mole) of 2-chloroethyl ethyl sulfide was added. The reaction mixture was heated to reflux for 5 hours. The mixture was then filtered and concentrated under vacuum. The residue was dissolved in chloroform, washed with two 100 ml portion of water and dried over anhydrous magnesium sulfate. The solvent was then removed under vacuum to yield 28 g. (53 % of 79% pure) desired product as shown by its nuclear magnetic resonance (nmr) spectrum.

Analyses·Calculated for $C_8H_{19}O_2PS_3$; C, 35.31 ; H, 6.93; P, 11.31. Found: C, 34.82; H, 6.99; P, 11.15.

Example 2 — O-Ethyl S-1-Propyl S'-2-n-Propylthioethyl Dithiophosphate

According to the procedure described in Example 1, 35.7 g. (0.15 mole) of potassium O-ethyl S-1-propyl dithiophosphate and 20.8 g. (0.15 mole) of 2-chloroethyl n-propyl sulfide were reacted to yield 29 g. (50% of 79% pure) desired product as shown by its nmr spectrum.

Analyses·Calculated for $C_{10}H_{23}O_2PS_3$: C, 39.73; H, 7.61; P, 10.26 Found: C, 39.67; H, 7.80; P, 9.82.

Example 3 — O-Ethyl S-1-Propyl S'-2-i-Propylthioethyl Dithiophosphate

According to the procedure described in Example 1, 69.3 g. (0.5 mole) of 2-chloroethyl-i-propyl sulfide and 119.0 g. (0.5 mole) of potassium O-ethyl S-1-propyl dithiophosphate were reacted to yield 120.5 g. (80%) of desired product.

Analyses·Calculated for $C_{10}H_{23}O_2PS_3$: C, 39.73, H, 7.61; P, 10.26; S, 31.79. Found: C, 39.65; H, 7.45; P, 9.70; S, 32.47.

Example 4 — O-Ethyl S-1-Propyl S-2-Phenylthioethyl Dithiophosphate

According to the procedure described in Example 1, 23.8 g. (0.1 mole) of potassium O-ethyl S-1-propyl dithiophosphate and 17.3 g (0.1 mole) of 2-chloroethyl phenyl sulfide were reacted to give 13.0 g. (39%) of the desired product as shown by its nmr spectrum.

Analyses·Calculated for $C_{13}H_{21}O_2PS_3$: C, 46.49; H, 6.25; P, 9.23. Found: C, 46.13; H, 6.07; P, 8.86.

Example 5 — O-Ethyl S-1-Propyl S'-2-p-Chlorophenylthioethyl Dithiophosphate

A solution of 49.8 g. (0.24 mole) of 2-chloroethyl 4-chlorophenyl sulfide and 57.0 g. (0.24 mole) of potassium O-ethyl S-1-propyl dithiophosphate in 500 ml of dimethyl formamide (DMF) was heated to 74° C. for 24 hr. The mixture was cooled to ambient temperature and diluted with 2 liters of chloroform. The solution was then extracted with four 1 liter portions of water. The chloroform solution was dried over anhydrous magnesium sulfate and chloroform was removed under vacuum. The residue was heated to 95° at 0.04 mm pressure to remove traces of DMF. The desired product was obtained in 50% yield (44.9 g.)

Analyses·Calculated for $C_{13}H_{20}ClO_2PS_3$: C, 42.05; H, 5.39; P, 8.36; S, 25.88. Found: C, 42.69; H, 5.20; P, 5.53; S, 25.58.

Example 6 — O-Ethyl S-1-Propyl S'-2-Methylsulfinylethyl Dithiophosphate

O-Ethyl S-1-propyl S'-(2-methylthioethyl) dithiophosphate (876.8 g., 3.2 moles) was dissolved in 1 liter of acetic acid. A solution of 120 ml. of conc. sulfuric acid in 397 g. (3.5 moles of 30%) hydrogen peroxide was added dropwise maintaining the temperature between 10°–20° C. The reaction mixture was left to stir at ambient temperature for 13 hours. Two liters of chloroform were added to extract the dithiophosphate. The organic layer was then extracted with three 1-liter portions of water. Subsequently, the solution was washed with 5% aqueous sodium hydrogen carbonate until neutral. Then, it was dried over anhydrous magnesium sulfate and filtered with suction. The solvent was then removed under vacuum to yield 862 g. of 73% pure desired product. The structure was proven by its nmr spectrum.

Example 7 — O-Ethyl S-1-Propyl S'-(2-Methylsulfonylethyl) Dithiophosphate

O-Ethyl-S-1-propyl S'-(2-Methylsulfonylethyl) Dithiophosphate

O-Ethyl S-1-propyl S'-(2-methylthioethyl) dithiophosphate (54.8 g., 0.2 mole) was mixed with 50 ml of water. Potassium permanganate (42.0 g., 0.25 mole) and 7.2 ml. of conc. sulfuric acid were dissolved in 500 ml of water. The solution was added dropwise to the stirred phosphate ester mixture while maintaining the temperature between 15°–20° C. The reaction mixture was filtered and the filtrate was treated with sodium bisulfite to remove the excess potassium permanganate. The mixture was then saturated with sodium sulfate and extracted with two 100 ml portions of dichloromethane. The combined organic extracts were then dried over anhydrous magnesium sulfate and filtered. The solvent was then removed under vacuum to yield 13 g. (21%) of the desired product. The assumed structure of the product was supported by its nmr spectrum.

Example 8 — O-Ethyl S-1-Propyl S'-2-i-Propylsulfinylethyl Dithiophosphate

According to the procedure of Example 6, 60.4 g. (0.2 mole) of O-ethyl S-1-propyl S'-2-i-propylthioethyl phosphorodithioate were reacted to yield 59 g. of 87% pure desired product.

Analyses·Calculated for $C_{10}H_{23}O_3PS_3$: P, 9.74. Found: P, 9.49.

Example 8 — O-Ethyl S-1-Propyl S'-2-Methylsulfonylpropyl Dithiophosphate

O-Ethyl S-1-propyl S'-2-methylthiopropyl dithiophosphate (83.0 g., 0.29 mole) was treated according to the procedure outlined in Example 7 to yield 13.1 g. (14%) of the desired product as shown by its nmr spectrum. Example 10 — O-Ethyl S-t-Butyl S'-2-Ethylthioethyl Dithiophosphate Equimolar amounts of O,O'-diethyl dithiophosphoric acid and isobutylene were heated in Pyrex glass pressure tube at 50° C. Analyses of periodically taken samples of the mixture by nuclear magnetic resonance spectroscopy has shown a rapid ionic addition took place in a Markovnikov-manner to form O,O'-diethyl S-t-butyl dithiophosphate ester. Distillation in vacuo of the mixture of one mole of each of the reactants after 24 hours yielded 192 g. (82%) of the ester product, having a boiling range of 108°–9° at 0.1 mm pressure.

For a selective O-dealkylation of the above ester intermediate, potassium hydrogen sulfide reagent was prepared by introducing hydrogen sulfide gas until saturation at 0° C. into the stirred solution of 41 g. (0.73 mole) of potassium hydroxide in absolute ethanol. Into the stirred solution of the dealkylating reagent, 167.4 g. (0.69 mole) of the ester was added below 20° C. The reaction mixture was then refluxed for 5 hours. A sample of the reaction mixture was then extracted with a fourfold volume of ether and the solvent evaporated in vacuo to determine the amount of unconverted ester. A conversion of 70% of the ester was indirectly indicated in this manner. The product of the reaction was isolated by removing the ethanol solvent in vacuo, dissolving the salt in 400 ml. of water, and extracting out the uncoverted ester with 200 ml. of diethyl ether. The water solution of the salt was then concentrated to 200 ml. in a film evaporator. The residual water of the salt was removed by azeotropic distillation in vacuo with 200 ml. ethanol. The ethanolic concentrate was crystallized at −25° C., filtered cold, washed with ether and dried in vacuo in yield the salt. Nmr analysis of the salt in deutermethanol solution showed that it was O-ethyl S-t-butyl dithiophosphoric acid potassium. The amount of the crystalline salt of m.p. 199°–200° C. (29 g.) corresponds to 24% of the yield calculated for 70% conversion.

In order to synthesize the final ester product, to 25.2 g. (0.1 mole) of the salt suspended in 82 g. (2.0 mole) of acetonitrile 12.5 g. (0.1 mole) of 2 chloroethyl ethyl sulfide was added dropwise with stirring. The stirred mixture was heated at 60° C. for 2 hours to effect the chlorine displacement reaction. Thereafter, the acetontrile was removed in vacuo at 50° C. and the residual product taken up in 150 ml. benzene. The unconverted salt and any acidic impurity were removed by washing with 75 ml. water and then with 50 ml. 5% aqueous sodium hydrogen carbonate solution. The benzene solution of the ester was then dried over sodium sulfate and filtered. After the removal of most of the benzene at 50° C. at pressures down to 26 mm, all unconverted chloroethyl ethyl sulfide was removed at 0.05 mm at 25° C. in 4 hours. The expected structure of the residual yellow liquid product was confirmed by nmr. The quantity (23 g.) of the product obtained was 60% of the theoretical yield.

Analyses·Calculated for $C_{10}H_{23}O_2PS_3$: C, 39.72; C, 39.72; H, 7.66; P, 10.24; S, 31.81. Found: C, 39.90; H, 7.42; P, 9.69; S, 31.53.

The S-ethylthioethyl O-ethyl S'-t-butyl dithiophosphate product is thermally highly unstable due to the presence of the S-tertiary butyl group. For example, it is decomposed to yield isobutylene on attempted gas chromatographic analyses at an injector temperature of 200° C. The corresponding primary alkyl derivatives such as the S'-n-propyl compound are stable under similar conditions.

The product cannot be prepared via known methods, i.e. by the reaction of a S-ethylthioethyl O-ethyl dithiophosphate salt with t-butyl chloride or bromide.

Example 11 — O-Ethyl S-1-Propyl S'-Ethylthiomethyl Dithiophosphate

O-Ethyl S-n-propyl dithiophosphoric acid potassium salt (23.8 g., 0.1 mole), prepared as described under Example 1, was suspended by stirring in 41 g. (1 mole) of acetonitrile. To the stirred salt suspension, 11.05 g. (0.1 mole) of chloromethyl ethyl sulfide was added dropwise. The reaction mixture was stirred overnight and then heated for 2 hours at 60° C. to complete the reaction. Thereafter, the acetonitrile was removed in vacuo at 50 and the residue was dissolved in a mixture of 150 ml. benzene and 75 ml. water. The resulting benzene solution of the crude product was then washed with 50 ml. 5% aqueous sodium hydrogen carbonate solution and then 50 ml. water. Then it was dried and evaporated. Finally, all the volatiles were removed by heating at 50° C. under 0.2 mm pressure. Nmr indicated that the residual product had the expected O-ethyl S-1-propyl S'-ethylthiomethyl dithiophosphate structure The amount of the yellow liquid product (24 g.) was 87% of the theoretical.

Analyses·Calculated for $C_8H_{19}O_2PS_3$: C, 35.02; H, 6.97; P, 10.54. Found: C, 35.44; H, 6.72; P, 10.52.

The above ethylthiomethyl ester (13.7 g.; 0.05 mole) was oxidized to the corresponding ethylsulfinylmethyl ester by the addition of a solution of 10.5 g. of 85% m-chloroperbenzoic acid (0.053 mole) in 100 ml. chloroform with stirring and ice-water cooling below 20° C. The mixture was allowed to come to room temperature and to stand for 2 hours to complete the oxidation. Then it was cooled to −20° C. to crystallize all the m-chlorobenzoic acid by-product and filtered cold. The filtrate was washed with 50 ml. 10% aqueous sodium carbonate solution and dried over sodium sulfate. After the removal of all the solvent and any other volatile compounds at 0.1 mm, the expected ethylsulfinylmethyl compound was obtained as indicated by nmr. The residual product was 11 g. (76%) clear, yellow liquid.

Analyses·Calculated for $C_8H_{19}O_3PS_3$: C, 33.09; H, 6.59; P, 10.66; S, 33.13. Found: C, 33.91; H, 6.31; P, 9.66; S, 31.44.

Nmr Analyses indicated that the ethylthiomethyl and the ethyl sulfinylmethyl esters were unstable. The ethyl thiomethyl compound was slowly decomposing at 60° C. The ethyl sulfinylmethyl product was unstable at room temperature.

Example 12 — O-Ethyl S-Isobutyl S'Ethylthiomethyl Dithiophosphate 0,0'-Diethyl S-p-isobutyl dithiophosphate ester was dealkylated with alcoholic potassium hydrogen sulfide in the manner described in Example 10. After allowing the mixture to react overnight at room temperature, it was found that 24% of the ester remained unchanged. The O-ethyl S-isobutyl dithiophosphoric acid potassium salt product of the reaction was dissolved in 1000 ml. water. The unconverted ester was extracted with 500 ml. ether and water film evaporated. The salt residue again dissolved in 400 ml. water and again extracted with ether (200 ml.). The water was then azeotroped in vacuo with an equal volume of ethanol. The residual liquid was cooled to −20° C. to crystallize the salt product, which was filtered cold with suction and washed with a 20 to 1 ether-alcohol mixture. After drying in vacuo, 81 g. (57% of the yield calculated on the basis of the conversion) salt of m.p. 201–3° C. was obtained. The O-ethyl, S-isobutyl dithiophosphate salt structure of the salt was confirmed by nmr in deuteromethanol.

In order to synthesize the final ester product, 25.2 g. (0.1 mole) of the above salt ws reacted with 11.05 g. (0.1 mole) of chloromethyl ethyl sulfide in the manner described in Example 11. The product as expected was 24 g. (83%) O-ethyl S-isobutyl S'-ethylthiomethyl dithiophosphate, which was a colorless clear liquid. Analyses·Calculated for $C_9H_{21}O_2PS_3$: C, 37.48; H, 7.33; P, 10.74. Found: C, 37.64; H, 7.25; P, 10.74.

The above ethylthiomethyl ester (13.7 g., 0.05 mole) was oxidized to the corresponding ethylsulfinylmetyl ester by 10.5 g. of 85% m-chloroperbenzoic acid in the manner described in Example 11: As shown by nmr the product was O-ethyl S-isobutyl S'-ethylsulfinylmethyl dithiophosphate. It was obtained as a clear yellow liquid in a 70% yield (10.5 g.)

Analyses·Calculated for $C_9H_{21}O_3PS_3$: C. 35.51; H, 6.95; P, 10.17; S, 31.60. Found: C, 33.58; H, 6.08; P, 9.40; S. 33.00.

Both the ethylthiomethyl and the ethylsulfinylmethyl ester products of the present example showed the thermal instability characteristics described for the corresponding products of Example 11.

Example 13—O:ETHYL S-1-PROPYL S-2-ACETYLTHIOPROPYL DITHIOPHOSPHATE

O-Ethyl S-b 1-propyl S'-propenyl dithiophosphate (7.2 g., 0.03 mole) was placed in a quartz tube and cooled to −78° C. An excess of thiolacetic acid (5.0 g.) was added and the tube was then evacuated to 0.1 mm. The tube placed in a watr bath at 15° C. and was irradiated with ultraviolet light from three 100 watt Hanau lamps for 48 hours. The contents of the tube were dissolved in 250 ml of ether and washed with 100 ml of water and 50 ml of 5% sodium bicarbonate. The ether solution was then dried over anhydrous magnesium sulfate. The solvent was removed under vacuum and the residue was heated to 80° C. at 0.1 mm for 2 hours to yield 4.7 g. (50 %) of desired product.

Analyses.Calculated for $C_{10}H_{21}O_3PS_3$: P, 9.80. Found: P, 9.38.

This acyl substituted S-alkylthioalkyl dithiophosphate also shows the broad pesticidal spectrum and the specific activity against Lepidoptera which is a characteristic of the hydrocarbyl substituted derivatives of the present invention.

General Experimental Procedures For Biological Testing of S-Hydrocarbylthioalkyl O,S'-Dialkyl Dithiophosphates In Examples 14–29 which follow, the new dithiophosphate compositions of the present invention were tested in the greenhouse and in the laboratory to determine their biological activity. Structurally related, known compounds, usually leading cmmercial compounds, were also tested side-by-side to determine the relative pesticidal effectiveness of the new compounds.

In the insecticidal and miticidal tests, the experimental compounds were tested as aqueous emulsions. These emulsions were prepared by dissolving the compound in acetone and dispersing it in distilled water with Triton X-100, an alkylaryl polyether alcohol derived by the reaction of i-octylphenol with ethylene oxide, to give spray emulsions containing the desired concentrations of the compound. These emulsions were then used in standard laboratory tests described below.

Insecticidal and Miticidal and Nematocidal Tests

Mexican Bean Beetle: Bean leaves were dipped in the emulsion of the test chemical and allowed to dry. Individual treated leaves were placed in Petri dishes and four Mexican bean beetle larvae introduced into each of the two replicate dishes.

Southern Army Worm: Bean leaves were dipped in a formulation of the test chemical and allowed to dry. Individual treated leaves were placed in Petri dishes and four Southern Army Worm larvae introduced into each of two relicate dishes.

Mites, Contact: Potted bean plant infested with the two-spotted spicer mite were placed on a turntable and sprayed with a formulation of the test chemical. The plants were held for 5 days and the degree of mite control was rated after 2 days.

Mite, Systemic: Bean plants infested with the two-spotted mites were treated by applying 20 ml. of the formulated test chemical to the soil.

Aphid, Contact: Potted nasturtium plants infested with the bean asphids were placed on a turntable and sprayed with a formulation of the test chemical. The plants were held for 2 days and the degree of aphid control was rated.

Aphid, Systemic: Nasturtium plants infested with the bean aphid were treated by applying 20 ml. of the formulated test chemical to the soil. The degree of aphid control was rated after 2 days.

Housefly: Caged houseflies are sprayed with the formulated test chemical. After 2 days the degree of housefly control was rated.

Corn Root Worm: This test was done in the soil with larvae 7-10 days old in the following manner. Seventy-five ml. (90-100 grams) of an air dried soil-sand (2:1) mixture was placed in an 8ounce plasticized cup. Ten ml. of a 55 ppm. stock equivalent to 5 ppm. in soil or 10 pounds in a 6-inch deep acre, was pipetted onto the surface of the soil. The cup was capped and one hour later it was shaken vigorously thirty times. The cup was removed and two very young corn plants and five larvae were introduced. Readings on mortality were made five days later.

Root-knot Nematode: An air-dried 2:1 soil-sand mixtue (125 ml.) in an 8-ounce plasticized container was infested with a stock of root-knot nematode prepared 7-10 days previously (at the rate of 6-7 grams of chopped galls per gallon of soil). Ten ml. of the formulated test chemical at 231 ppm. was poured onto the surface of the soil-sand mixture to give a rate equivalent to 25 pounds per 6 inch acre. The container was then capped and shaken vigorously 1 hour later. The container was kept for 5-7 days, then shaken again, and seeded with 4 cucumber seeds by placing the seeds on the surface and covering with ½ inch of sand. After 3-4 weeks the roots were examined for galls and the degree of control determined.

Bollworms: Bollworm larvae used in the present study were progeny of adult moths collected from light traps stationed in cotton fields. The larvae were reared on the Vanderzant-Adkisson Special Wheat Germ Diet for Insects. This diet was fortified with Vanderzant's Insect Vitamin Fortification. The diet and the vitamin fortification were obtain from Nutritional Biochemicals Corporation, Cleveland, Ohio. The larvae were reared and tested in continuous illumination at 78±5° G. Only third and fourth instar larvae which weighed between 25 and 60 mg. were used in the tests.

Insecticidal sprays were made by the conventional low-volume (CLV) method. CLV sprays were applied through a 6X hollow-cone nozzle calibrated to deliver the equivalent of 3.5 ga./acre of the water/emulsion spray mixture. Sprays were applied to individual cotton plants grown in one gallon buckets. After treatment the plants were allowed to dry for 1 to 2 hours in the open air before being transported to a holding room. The larvae were placed on the treated leaf surfaces and held singly in small snap-on type plastic screen cages of about 1½ inches in diameter. Untreated control groups were maintained for each test replicate so that treatment mortalities could be adjusted according to Abbott's formula. Treatments were replicated 3 times. Each replicate contained 20 larvae. Mortality records were made 48 hours after treatment.

Cholinesterase Inhibition: To a solution of 0.2 unit of bovine cholinesterase in 2.97 ml. of a buffer solution containing 11.15 grams of disodium hydrogen phosphate dodecahydrate and 1.81 grams of potassium dihydrogen phosphate per liter of water, 0.03 ml. of a solution of the test chemical in acetone was added. This mixture was then incubated in a water bath at 35° C. for 30 min. One ml. of a solution containing 100 milligrams of 5,5'-dithiobis-(2-nitrobenzoic acid), 100 milligrams of acetylthiocholine iodide, and 75 ml. of the above buffer solution in sufficient water to make 200 ml. was then added and the mixture again incubated in a water bath at 35° C. for 30 minutes more. The amount of inhibition of bovine chloinesterase was then determined from the absorbance of this solution at 420 m$\mu$ (millimicron). By using a series of solutions of the test chemical at various concentrations in acetone, the concentration needed for 50% inhibition was determined.

The insecticidal effectiveness of organophosphorus compounds is generally attributed to chlorinesterase inhibition. Determination of the chlorinesterase inhibition is widely used to estimate the insecticidal potential of new organophosphorus compounds.

Fungicidal Tests

Bean Powdery Mildew: Bradicant Test

In these tests, the experimental compounds were tested in aqueous emulsions, prepared in the same manner as was previously described above with respect to the insecticidal and miticidal tests.

Bean plants with fully expanded primary leaves were inoculated with spores of the powdery mildew fungus (Erysiphe Polygoni). Emulsions of the experimental chemicals were then sprayed on the plants placed on the revolving turntable. The plants were then kept in a greenhouse for 7 to 10 days. The amounts of the mildew on their primary leaves were then rated.

Bean Ruts: Eradicant Test

Pinto bean plants with fully expanded primary leaves were inoculated with spores of the bean rust fungus (Uromyces Phaseoli) and incubated for 24 hours. The test were then carried out as described above for Bean Powdery Mildew.

Bean Rust: Systemic Eradicant Test

Pinto bean plants were inoculated 24 hours prior to use as above and the soil in the pot was then treated with 20 ml. of an emulsion of the test chemical. The rest of the test and the evaluation were then carried out an above for Bean Powdery Mildew.

Sclerotium: SOil Fungicide Test

Sterilized soil was inoculated with Solerotium and placed into a 4-ounce "Dixie cup", and drenched with 20 ml. of an emulsion of the test chemical. The cup was then incubated for 2 days at 70° F. Thereafter, the amount of mycelial growth on the soil surface was rated and the control by the chemical estimated accordingly.

Animal Systemic Insecticide Tests

The experimental compounds, formulated as 5% solutions in Tween 20, were administered orally and subcutaneously to guonea pigs which have been artificially infested with nymphs of the lone star tick at 48 hours before treatment, larvae of the secondary screw worm and of the black blow fly at 24 hours before treatment. Mortality was observed 24 hours after the treatment. For the details of the techniques, reference is made to the publications of R. O. Drummond in the Journal of Economic Entomology, particularly in Vol. 60, pages 733–737 in 1967.

Acute Oral Toxicity Tests on Rats

Each compound tested was administered orally by stomach tube to five to eight groups of five male albino rate of the Sprague Dawley strain, weighing 220 to 300 grams at various dosage levels. Following incubation, the animals were closely observed for mortality and toxic effects at intervals for 14 days. Statistical analysis of the mortality data was carried out to determine the median lethal dosages ($LD_{50}$) according to the method of W. R. Thompson as described in the Journal Bact. Rev. in Vol. 11, pages 115–145 in 1947, utilizng the tables of H. J. Horn published in the Journal Biometrics, Vol. 12, page 311 in 1956. The $LD_{50}$ dosages are expressed in mg weights of test material per kg weight of rat used.

Example 14—The Effect of the Introduction OF S-n-Propyl Group into Commercial O,O'-Dithyl S-Hydrocarbylthioalkylk Dithiophosphate Pesticides A number of leading commercial O,O'-diethyl S-hydrocarbylthioalkyl diethophosphate pesticides were converted to the correspondng O-ethyl-S-n-propyl S'-hydrocarbylthioalkyl dithiophosphates using the present process as described in Examples 2–4 of the parent application. The pesticidal activity of the starting commercial compounds was then compared with that of the corresonding O,S-isomers in order to determine the effect of the introducton of the S-n-propyl group. The data resulting are given in Table I below.

TABLE I

Effect of the Introduction of the S-Propyl Group Into Commercial O,O-Diethyl S-Hydrocarbylthioalkyl Pesticides $$\begin{array}{c} C_2H_5O \\ \diagdown \\ \phantom{n\text{-}C_3H_7S} P-S-(CH_2)_{1-2}-SR_1 \\ \diagup \phantom{\|} \| \\ n\text{-}C_3H_7S \phantom{P-}O \end{array}$$

| Experimental Compound (Example No. or Trade Name) | Southern Army Worm Conc. ppm | Southern Army Worm Mortality, % | Mexican Bean Beetle Larvae Conc. ppm | Mexican Bean Beetle Larvae Mortality, % | House Fly Spray Mortality, % (at 20 ppm) | Corn Rootworm Larvae Mortality, % (at 2.5 ppm) | Nematodes Rate, Control % after 1–4 weeks (at 25#/acre) | Cholinesterase Inhibiting conc. $LD_{50}$, Mole/Liter |
|---|---|---|---|---|---|---|---|---|
| $C_2H_5O\diagdown$<br>$\phantom{n\text{-}C_3H_7S\diagup}P(O)-SCH_2CH_2SC_2H_5$<br>$n\text{-}C_3H_7S\diagup$<br>(30) | 50 | 100 | 50 | 100 | 100 | 20 | 100 | $1.1 \times 10^{-6}$ |
| $(C_2H_5O)_2P(S)SCH_2CH_2SC_2H_5$<br>(Disyston) | 50 | 0 | 50 | 30 | 100 | 0 | 0 | $3.8 \times 10^{-4}$ |
| $C_2H_5O\diagdown$<br>$\phantom{n\text{-}C_3H_7S\diagup}P(O)-SCH_2SC_2H_5$<br>$n\text{-}C_3H_7S\diagup$<br>(11) | 100 | 100 | 100 | 100 | 100 | 100 | 100 | $2.7 \times 10^{-6}$ |
| $(C_2H_5O)_2P(S)SCH_2SC_2H_5$<br>(Thimet) | 100 | 0 | 100 | 90 | 90 | 100 | 0 | $3.1 \times 10^{-5}$ |
| $C_2H_5O\diagdown$<br>$\phantom{n\text{-}C_3H_7S\diagup}P(O)SCH_2S\text{-}\text{Ar}\text{-}Cl$<br>$n\text{-}C_3H_7S\diagup$<br>(31) | 100 | 100 | 100 | 100 | $100^a$ | 0 | 100 | $4.1 \times 10^{-9}$ |
| $(C_2H_5O)_2P(S)SCH_2S\text{-}\text{Ar}\text{-}Cl$<br>(Trithion) | 100 | 0 | 100 | 90 | $80^a$ | — | — | $7.9 \times 10^{-4}$ |

The data show that the present process resulted in superior pesticides. The increase of activity on isomerization is believed particularly apparent in the case of the Southern army worm. The increased pesticidal activity, in general, is believed to be apparently related to the increased effectiveness of the isomeric compounds as cholinesterase inhibitors.

An increase of the pesticidal activity is considered to be very surprising since a change from the ethyl to the propyl esters of thio- and dithiophosphorus acids is usually accompanied by a decrease of their effectiveness, as discussed in Schrader monograph previousy mentioned.

Example 15 – The Effect of S-Ethyl Versus S-n-Propyl Group on the Pesticidal Activity The O,S-dialkyl S-2-alkylthiopropyl dithiophosphates were selected for a study of correlations between chemical structure and biological activity.

In Table II below, the effect of S-ethyl versus the S-n-propyl group is shown on the insecticidal, miticidal and nematocidal activity of the corresponding O-ethyl S-2-ethylthiopropyl dithiophosphate esters. The data show that the S-n-propyl compound is an effective insecticide at 50 ppm while the S-ethyl compound shows no activity at this concentration.

Table III shows the fungicidal activity of the same two compounds. The data show that the S-n-propyl compound is again active at concentrations where the S-ethyl compound shows no sign of activity.

Example 16 – The Effect of the Structure of the Higher S-Alkyl Groups on the Pesticidal Activity After finding that the substitution of the O-ethyl by the S-n-propyl group increases pesticidal activity, the effect of other higher S-alkyl groups was examined. The results are shown in Table IV.

The results show that all the $C_3$-$C_4$ S-alkyl compounds have superior pesticidal activity to the known $C_1$-$C_2$ S-alkyl compounds. The activity of the S-n-propyl compound was found to be the best, followed, in decreasing order of activity, by the S-isobutyl, the S-i-propyl and the S-n-butyl compounds.

Example 17 – The Effect of Primary versus Tertiary S'-Alkyl Group on the Pesticidal Activity After finding that the primary and secondary $C_3$-$C_4$ S-alkyl compounds had superior pesticidal activity, a comparison was made between analogous compounds having S-n-propyl and S-t-butyl substituents. The results of testing these compounds against Southern armyworm of the order of Lepidoptera are shown in Table V. The data indicate that the activity is adversely affected by changing a normal alkyl for a tertiary alkyl group.

TABLE II

The Effect of the S-Ethyl versus the S-n-Propyl Group on the Pesticidal Activity of O-Ethyl S-2-Ethylthiopropyl Dithiophosphate Esters

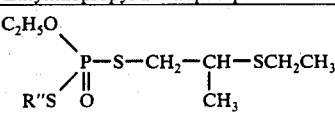

| Experimental Compound | | | Pest Control, % | | | | | | | |
|---|---|---|---|---|---|---|---|---|---|---|
| | | | Routine Insecticidal and Miticidal Tests | | | | | | Corn | Nematode |
| Example No. | R'' | Conc. ppm | S. Army Worm | Mex. Bean Beetle | Spider Mites Contact | Spider Mites Systemic | Bean Aphids Contact | Bean Aphids Systemic | Rootworm (0.25 ppm) | Control (25 lb/acre) |
| 29 | $C_2H_5$ | 250 | 0 | 50 | 90 | 50 | 80 | 0 | 20 | 20 |
| | | 50 | 0 | 0 | 0 | 0 | 0 | 0 | — | — |
| 33 | n-$C_3H_7$ | 250 | 100 | 100 | 100 | 100 | 100 | 100 | 100 | 100 |
| | | 50 | 100 | 100 | 100 | 100 | 100 | 0 | — | — |

TABLE III

The Effect of the S-Ethyl versus the S-n-Propyl Group on the Fungicidal Activity of O-Ethyl S-2-Ethylthiopropyl Dithiophosphate Esters

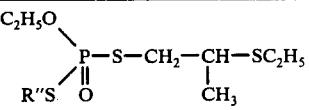

| Experimental Compound | | Control of Foliar Fungi, % (at 200 ppm) | | | Control of Sclerotium, % |
|---|---|---|---|---|---|
| Example No. | R'' | Bean Mildew Eradicant | Bean Rust Eradicant | Bean Rust Systemic Eradicant | (at 100 lb/acre) |
| 29 | $C_2H_5$ | 0 | 0 | 0 | 0 |
| 33 | n-$C_3H_7$ | 70 | 80 | 90 | 60 |

Table V

The Effect of Substituting S-Primary Alkyl for an S-Tertiary Alkyl Group on the Activity of O-Ethyl S-2-Ethylthiopropyl Dithiophosphate Pesticides Against Lepidoptera

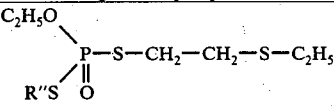

| Experimental Example No. | Compound R | Conc. ppm. | Mortality of Southern Armyworm, % |
|---|---|---|---|
| 30 | $CH_3CH_2CH_2$ | 100 | 100 |
| | | 50 | 80 |
| 10 | $(CH_3)_3C$ | 100 | 0 |
| | | 50 | 0 |

TABLE IV

The Effect of the Structure of the Higher S-Alkyl Groups on the
Activity of O-Ethyl S-Alkyl S'-2-Methylthiopropyl Dithiophosphate Pesticides

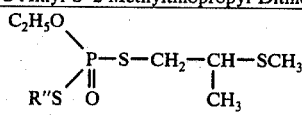

| Experimental Compound | | | | | Mortality Produced, % | | | | |
|---|---|---|---|---|---|---|---|---|---|
| Example No. | R" | Conc. ppm | S.Army Worm | Mex.Bean Beetle | Spider Mites Contact | Spider Mites Systemic | Bean Aphids Contact | Bean Aphids Systemic | House Flies |
| 32 | $CH_3CH_2CH_2$ | 250 | 100 | 100 | 100 | 100 | 100 | 100 | 100 |
|  |  | 50 | 100 | 100 | 100 | 100 | 100 | 0 | 100 |
| 42 | $(CH_3)_2CH$ | 250 | 100 | 100 | 100 | 100 | 100 | 80 | 100 |
|  |  | 50 | 0 | 100 | 100 | 0 | 50 | 20 | 0 |
| 41 | $CH_3CH_2CH_2CH_2$ | 250 | 0 | 100 | 100 | 100 | 100 | 40 | 100 |
|  |  | 50 | 0 | 80 | 100 | 0 | 60 | 0 | 0 |
| 37 | $(CH_3)_2CHCH_2$ | 250 | 80 | 100 | 100 | 100 | 100 | 100 | 100 |
|  |  | 50 | 0 | 100 | 60 | 100 | 10 | 70 | 45 |

Example 18 – Effect of the Structure of the O-Alkyl Groups on the Pesticidal Activity The effect of the O-alkyl groups was studied on the S-n-propyl S-methylthiopropyl dithiophosphate esters. The data are shown in Table VI below. They indicate that the presence of the O-ethyl group leads to the best overall activity. Although the systemic effectiveness of the O-methyl derivative is better because of its higher polarity, its general contact activity is lower. The O-n-propyl derivative shows the least activity both as a contact and as a systemic pesticide.

Example 19 – Effect of the Structure of the S-Alkyl Group of the Thioether Moiety on the Pesticidal Activity The effect of the structure of the S-alkyl thioether group was examined on the S-2-alkylthiopropyl esters of O-ethyl S'-n-propyl dithiophosphoric acid esters having optimized O,S'-dialkyl groups.

The data included in Table VII below show that the S-methyl, -ethyl and -n-propyl derivatives all have about the same pesticidal acitivity. Higher S-alkyl derivatives such as the S-n-hexyl compound, however, show a decreased level of activity. Overall, the activity is less sensitive to the alkyl variation in the thioether than in the phosphorus ester groups of the molecule.

TABLE VI

The Effect of the Structure of O-Alkyl Groups on the Pesticidal Activity
of O-Alkyl S-n-Propyl S-2-Methylthiopropyl Dithiophosphates

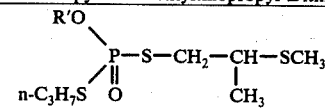

| Experimental Compound | | | | | Mortality Produced, % | | | | |
|---|---|---|---|---|---|---|---|---|---|
| Example No. | R' | Conc. ppm | S.Army Worm | Mex.Bean Beetle | Spider Mites Contact | Spider Mites Systemic | Bean Beetle Contact | Bean Beetle Systemic | House Flies |
| 40 | $CH_3$ | 250 | 100 | 100 | 100 | 100 | 100 | 100 | 100 |
|  |  | 50 | 0 | 0 | 100 | 100 | 100 | 100 | 100 |
| 32 | $CH_3CH_2$ | 250 | 100 | 100 | 100 | 100 | 100 | 100 | 100 |
|  |  | 50 | 100 | 100 | 100 | 100 | 100 | 0 | 100 |
| 43 | $CH_3CH_2CH_2$ | 250 | 0 | 100 | 100 | 100 | 80 | 20 | 100 |
|  |  | 50 | 0 | 80 | 50 | 0 | 80 | 0 | 70 |

TABLE VII

Effect of the Structure of the S-Alkylthioether Group on the Pesticidal
Activity O-Ethyl S-n-Propyl S-2-Alkylthiopropyl Dithiophosphates

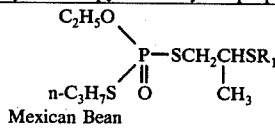

| Experimental Compound | | S.Armyworm Mortality,% (at 250 ppm) | Mexican Bean Beetles Mortality,% (at 50 ppm) | Spider Mites Mortality,% (at 10 ppm) | Bean Aphids Mortality,% (at 50 ppm) | Corn Rootworm Mortality,% (at 2.5 ppm) | Nematode Control,% (at 25 lb/acre) |
|---|---|---|---|---|---|---|---|
| Example No | $R_1$ | | | | | | |
| 32 | $CH_3$ | 100 | 100 | 100 | 100 | 100 | 100 |
| 33 | $C_2H_5$ | 100 | 70 | 100 | 100 | 100 | 100 |
| 34 | $n-C_3H_7$ | 100 | 100 | 100 | 100 | 100 | 100 |
| 35 | $i-C_3H_7$ | 100 | 100 | 100 | 50 | 70 | 100 |
| 36 | $n-C_6H_{13}$ | 100 | 100 | 90 | 50 | 0 | 10 |

Example 20 – The Effect of the S-Alkyl versus S-Aryl Group of the Thioether Moiety on the Pesticidal Activity The effect of the presence of the low S-alkyl versus S-aryl group was examined using the S-2-hydrocarbyl-thioethyl esters of O-ethyl S-n-propyl dithiophosphoric acid esters in a manner similar to the previous example.

The data given in Table VIII show again the $C_1$ to $C_3$ alkylthioether derivatives to all have about the same pesticidal activity. As far as systemic pesticidal effect is concerned, there is a slight drop in the case of the higher molecular weight propylthioether derivatives.

The contact insecticidal activity of the alkylthioether and arylthioether derivatives is similarly high. The aromatic derivatives do not show, however, a significant pest control via systemic action.

compound shows very little insecticidal activity at 50 ppm.

TABLE IX
Effect of the Structure of the Alkylene Group on the Pesticidal Activity of O-Ethyl S-n-Propyl S'-2-Methylthioalkyl Dithiopnosphates

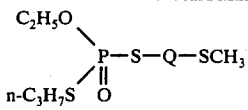

| Experimental Example No. | Compound Q | Mortality Produced at 50 ppm, % | | | | | Corn Rootworm Mortality, % at 2.5 ppm | Nematodes Control % at 25 lb/acre |
|---|---|---|---|---|---|---|---|---|
| | | Southern Army Worm | Mexican Bean Beetles | Spider Mites | Bean Aphids | House-flies | | |
| 44 | $CH_2CH_2CH_2$ | 100 | 100 | 100 | 100 | 100 | 0 | 90 |
| 32 | $CH_2CH(CH_3)$ | 100 | 100 | 100 | 100 | 100 | 100 | 100 |
| 38 | $CH_2CH(CH_2CH_3)$ | 80 | 10 | 100 | 100 | 100 | 40 | 90 |
| 39 | $CH_2CH[C(CH_3)_3]$ | 0 | 0 | 100 | 30 | 20 | 80 | — |

Example 22 — The Effect of the Oxidation of the Alkylthioether Group on the Pesticidal Activity Oxidized derivatives of the known S-hydrocarbylthioalkyl O,O'-dialkyl dithiophosphates are known to have

TABLE VIII
Effect of the Structure of the S-Hydrocarbylthioether Group on the Pesticidal Activity of O-Ethyl S-n-Propyl S-2-Hydro-Carbylthiopropyl Dithiophosphates

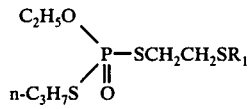

| Experimental Compound Example No. | $R_1$ | Mortality, %; Produced by an Emulsion of 250 PPM Concentration | | | | | | |
|---|---|---|---|---|---|---|---|---|
| | | Southern ArmyWorm | Mexican Bean Beetles | Spider Mites Contact | Systemic | Bean Aphids Contact | Systemic | House Flies |
| 1 | $CH_3$ | 100 | 100 | 100 | 100 | 100 | 95 | 100 |
| 30 | $C_2H_5$ | 100 | 100 | 100 | 100 | 100 | 90 | 100 |
| 2 | $n-C_3H_7$ | — | 100 | 100 | 100 | 90 | 75 | 100 |
| 3 | $i-C_3H_7$ | 100 | 100 | 100 | 85 | 70 | — | — |
| 4 | $C_6H_5$ | 100 | 100 | 100 | 40 | 95 | 20 | 95 |
| 5 | $p-C_6H_4Cl$ | — | 100 | 100 | 40 | 95 | 10 | — |

Example 21 — Effect of the Structure of the Alkylene Group on the Pesticidal Activity Known, commercial S-hydrocarbylthioalkyl, O,O''-dialkyl dithiophosphates have a methylene or an ethylene group for the alkylene part of the molecule. In Example 14 it has previously been shown that the O-ethyl S'-n-propyl dithiophosphate ester derivatives of these products are superior, novel pesticides. The effect of higher alkylene groups was also studied, using the present, novel O-lower alkyl S'-higher alkyl dithiophosphate esters. As an optimized structure type, O-ethyl S-n-propyl S'-methylthioalkyl dithiophosphate was selected for $C_3$ to $C_6$ alkylene variation. The results are shown in Table IX below.

The data indicate that the $C_3$ and $C_4$ alkylene groups lead to highly active compounds. The optimal alkylene group was found to have three carbon atoms. Alkylene groups having more than 4 carbon atoms show a definite drop in activity. For example, the t-butyl ethylene a higher pesticidal activity due to the oxidation of the thioether sulfur to the corresponding sulfoxide and/or sulfone. The effect of oxidizing the thioether group of the present S-hydrocarbylthioalkyl O,S'-dialkyl dithiophosphates is reported here. As an example, the pesticidal effect of several sulfoxide and sulfone derivatives obtained by the oxidation of O-ethyl S'-n-propyl S-alkylthioalkyl dithiophosphates is shown in Table X.

The data on the first three compounds of Table X show that the oxidation of such compounds does not produce a major change in their pesticidal effectiveness. At a concentration of 250 ppm, O-ethyl S'-n-propyl methylthioethyl dithiophosphate, the corresponding sulfoxide and sulfone compounds all provided essentially complete control of representative insects, mites and nematodes.

It is recalled from Examples 11 and 12 that the oxidized derivatives of similar alkylthiomethyl compounds are very unstable and as such are not desirable pesticides in economic use.

TABLE X

Effect of the Oxidation of the Alkylthioether Group on the Pesticidal Activity of O-Ethyl S-n-Propyl S'-2-Alkylthioalkyl Dithiophosphates

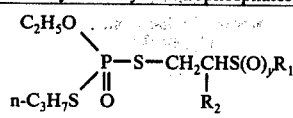

$$\begin{array}{c} C_2H_5O \\ \diagdown \\ \phantom{n\text{-}C_3H_7S}P-S-CH_2CHS(O)_yR_1 \\ \diagup \| \quad | \\ n\text{-}C_3H_7S \quad O \quad R_2 \end{array}$$

| Experimental Example No. | $R_1$ | $R_2$ | y | Mortality, %; Produced by an Emulsion of 250 ppm Concentration |||||| Nematode Control,% at 25 lb/acre |
|---|---|---|---|---|---|---|---|---|---|---|
| | | | | Southern ArmyWorm | Mexican Bean Beetle | Spider Contact | Mites Systemic | Bean Contact | Aphids Systemic | |
| 1 | CH$_3$ | H | 0 | 100 | 100 | 100 | 100 | 100 | 95 | 90 |
| 6 | CH$_3$ | H | 1 | 100 | 100 | 100 | 100 | 100 | 100 | 100 |
| 7 | CH$_3$ | H | 2 | 100 | 100 | 100 | 100 | 100 | 100 | 100 |
| 8 | CH(CH$_3$)$_2$ | H | 1 | 90 | 100 | 95 | 90 | 100 | — | 75 |
| 9 | CH$_3$ | CH$_3$ | 2 | 100 | 100 | 90 | 90 | 90 | 95 | 80 |

Example 23 — Effect of Various Types of O,S'-Dialkyl S-Hydrocarbylthioalkyl Dithiophosphates as Animal Systemic Insecticides The reduced toxicity of the present O,S'-dialkyl dithiophosphate derivatives, especially of the O-ethyl S'-n-propyldithiophosphates allows their testing as systemic insecticides on animals. The testing of various types of O-ethyl S'-n-propyl S-hydrocarbylthioethyl dithiophosphates was carried out using guinea pigs. The results are given in Table XI.

The data show that the alkylthioalkyl compounds, i.e., the first two, are active against the Arthropoda insects used at a dosage of 50 mg compound per kg pig. Both the thioether compound (1) and its sulfoxide analog have similar effectiveness. However, the corresponding arylthioalkyl compound shows no systemic insecticidal effect either on oral or subcutaneous administration at a dosage of 100 mg/kg.

toxicity of the S-n-propyl group which is the key group in attributing the pesticidal activity. The data are shown in Table XII below.

Studying the first three compounds, i.e., S-ethyl-thioethyl O-ethyl dithiophosphate derivatives, it was found that both the O,S-isomerization and replacement of an O-ethyl with an S-n-propyl group result in reduced toxicity. Using the process of the parent application, the new S-propyl compound with a median lethal dose, LD$_{50}$, of 318 mg/kg is produced from Disyston having a median lethal toxicity, LD$_{50}$, of 25 mg/kg.

Similarly, S-n-propyl derivatives of reduced toxicity can be derived from S-2-alkylthiopropyl O-ethyl dithiophosphate derivatives as shown by the compounds of Examples 6-8. The S-2-n-propylthiopropyl compound of Example 8 has a particularly low toxicity. The increasing size of the alkylthioether group apparently reduces the toxicity.

Compared to the O,O-diethyl derivatives, the O,S'-

TABLE XI

Effect of Types O-Ethyl S'-n-Propyl S-Hydrocarbylthioethyl Dithiophosphates on Their Systemic Insecticidal Activity in Guinea Pigs

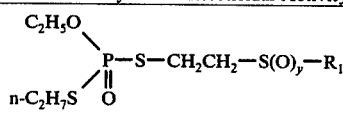

$$\begin{array}{c} C_2H_5O \\ \diagdown \\ \phantom{n\text{-}C_2H_7S}P-S-CH_2CH_2-S(O)_y-R_1 \\ \diagup \| \\ n\text{-}C_2H_7S \quad O \end{array}$$

| Experimental Compound ||| Method of Administration | Lowest Dosage (mg/kg) Causing Complete Kill of |||
|---|---|---|---|---|---|---|
| Example No. | Structure ||| | Nymphs of Lone Star Ticks | Larvae of ||
| | y | $R_1$ | | | Black Blow Flies | Secondary Screw Worms |
| 1 | 0 | CH$_3$ | Oral | 50 | 50 | 50 |
| | | | Subcut. | 50 | 50 | 50 |
| 6 | 1 | CH$_3$ | Oral | 50 | 50 | 100 |
| | | | Subcut. | 50 | 50 | 50 |
| 4 | 0 |  | Oral | >100 | >100 | >100 |
| | | | Subcut. | >100 | >100 | >100 |

Example 24 — The Effect of the S-n-Propyl Group on the Toxicity Towards Warm Blooded Animals The pesticidally effective novel O-ethyl S-n-propyl S'-alkylthioalkyl compounds were also examined for their acute, oral toxicity on rats. Conventional toxicity experiments were designed to determine the effect on diethyl dithiophosphates have generally much lower toxicity. The reduction of toxicity is largely independent of the structure of the hydrocarbylthioalkyl group.

It is most surprising and advantageous that within the present new class of compounds the highly effective pesticides have low toxicities.

TABLE XII

The Effect of the S-n-Propyl Group on the Toxicity Towards Warm Blooded Animals

| Experimental Compound Example No. (Reference) | Structure | Acute Oral Toxicity on Rats, Median Lethal Conc., $LD_{50}$ mg/kg |
|---|---|---|
| (Disyston[a]) | $C_2H_5O\!\!>\!\!P(\!=\!S)(OC_2H_5)\!-\!SCH_2CH_2SC_2H_5$ | 25 |
| (a) | $C_2H_5O\!\!>\!\!P(\!=\!O)(SC_2H_5)\!-\!SCH_2CH_2SC_2H_5$ | 100 |
| 30 | $C_2H_5O\!\!>\!\!P(\!=\!O)(S\text{-}n\text{-}C_3H_7)\!-\!SCH_2CH_2SC_2H_5$ | 318 |
| (b) | $C_2H_5O\!\!>\!\!P(\!=\!S)(OC_2H_5)\!-\!SCH_2CH(CH_3)SCH_3$ | 25 – 50 |
| 32 | $C_2H_5O\!\!>\!\!P(\!=\!S)(S\text{-}n\text{-}C_3H_7)\!-\!SCH_2CH(CH_3)SCH_3$ | 109 |
| (b) | $C_2H_5O\!\!>\!\!P(\!=\!S)(OC_2H_5)\!-\!SCH_2CH(CH_3)SC_2H_5$ | 25 – 50 |
| 33 | $C_2H_5O\!\!>\!\!P(\!=\!O)(S\text{-}n\text{-}C_3H_7)\!-\!SCH_2CH(CH_3)SC_2H_5$ | 214 |
| 2 (CIP) | $C_2H_5O\!\!>\!\!P(\!=\!O)(S\text{-}n\text{-}C_3H_7)\!-\!SCH_2CH_2SC_3H_7\text{-}n$ | 215 |
| 34 | $C_2H_5O\!\!>\!\!P(\!=\!O)(S\text{-}n\text{-}C_3H_7)\!-\!SCH_2CH(CH_3)SC_3H_7\text{-}n$ | 422 |

(a) Described in German Patent 1,032,247
(b) Synthesis described in French Patent 1,509,248

TABLE XIII

Effect of Oxidation on the Toxicity of O-Ethyl S-n-Propyl S'-Methylthioethyl Dithiophosphate $$C_2H_5O\!\!>\!\!P(\!=\!O)(S\text{-}n\text{-}C_3H_7)\!-\!S\!-\!CH_2CH_2\!-\!S(O)_y\!-\!CH_3$$

| Experimental Compound No. | y | Acute Oral Toxicity on Rats, Median Lethal Dosage, $LD_{50}$ mg/kg |
|---|---|---|
| 1 | 0 | 46 |
| 6 | 1 | 46 |
| 7 | 2 | >100 |

The results show that the oxidation to the sulfoxide does not change the toxicity of the hydrocarbylthioalkyl compound. The oxidation to the sulfone seems to decrease the toxicity as indicated by increasing median lethal dosage. These results on our O,S'-dialkyl dithiophosphate derivatives are surprising since the oxidation of O,O'-dialkyl dithiophosphates of similar structure, as reported by Schrader, resulted in increased rather than decreased toxicities.

Thus, a comparison of O-ethyl S'-n-propyl dithiophosphate derived sulfoxides and sulfones with the corresponding known sulfoxides and sulfones and sulfoxides of the O,O-diethyl dithiophosphates shows an unexpected difference in toxicities in favor of the compounds of this invention.

Example 26 Special Insecticidal Test Using O-Ethyl S'-n-Propyl-S-Hydrocarbylthioalkyl Dithiophosphates Many special insecticidal tests were carried out against difficult to control pests with the most active of the compositions of the present invention. This example describes the results of a test on bollworms grown on cotton. The test procedure was given with the other laboratory test descriptions. The results are shown by Table XIV.

The data of the table indicate a practically complete control of the bollworms by different types of alkylthioalkyl derivatives when applied at rate corresponding to a 0.5 lbs. active compound per acre application.

TABLE XIV
Control of Bellworms by O-Ethyl S'-n-Propyl S-Alkylthioalkyl Dithiophosphates

| Experimental Compound (Applied at 0.5 lbs/acre) | Per Cent Mortality (hours After Application) | | |
|---|---|---|---|
| | 24 | 48 | 72 |
| $\begin{array}{c}C_2H_5O\\ \diagdown\\ \phantom{xx}P-SCH_2CH_2SCH_3\\ \diagup \|\\ n\text{-}C_3H_7S \phantom{x} O\end{array}$ | 72 | 80 | 89 |
| $\begin{array}{c}C_2H_5O\\ \diagdown\\ \phantom{xx}PSCH_2CHSCH_3\\ \diagup \| \phantom{xxx} \|\\ n\text{-}C_3H_7S \phantom{x} O \phantom{xx} CH_3\end{array}$ | 84 | 96 | 96 |
| $\begin{array}{c}C_2H_5O\\ \diagdown\\ \phantom{xx}PSCH_2CHSC_3H_7\text{-}n\\ \diagup \| \phantom{xxx} \|\\ n\text{-}C_3H_7S \phantom{x} O \phantom{xx} CH_3\end{array}$ | 87 | 94 | 99 |

Pesticidal Field Testing of O-Ethyl S'-n-Propyl S-Hydro-Carbylthioalkyl Dithiophosphates Some of the most active O-ethyl S-n-propyl dithiophoshate esters of the present invention were extensively field tested. The field tests were carried out to demonstrate the effectiveness of derivatives having various types of hydrocarbylthioalkyl substituents under field conditions. Due to the nature of these tests minor differences in effectiveness are not necessarily connected with the structure variation.

Example 27 — Control of Corn Earworm by O-Ethyl S'-n-Propyl S-Methylthioalkyl Dithiophosphates Spring Gold sween corn was planted on March 21. Each treatment was made on a 48 ft. row and was replicated three times. Ratings represent the total counts from all three replicates. Except for insecticide treatment the plots were managed according to recommended farming practice for the area. Application of the experimental compositions at the 1 lb. active ingredient per acre were made and readings were made to determine the number of infested corn ears. The data are given in Table XV.

The results show an excellent control of corn earworm on the treated rows in contrast to the heavy infestation of the untreated check rows.

TABLE XV
Field Control of Corn Earworm By O-Ethyl S'n-Propyl S-Alkylthioalkyl Dithiophosphates

| Experimental Compound (Applied at 1 lbs/acre) | Number of Infested Corn Ears (150 Ears Sampled) |
|---|---|
| $\begin{array}{c}C_2H_5O\\ \diagdown\\ \phantom{xx}P-SCH_2CH_2SCH_3\\ \diagup \|\\ n\text{-}C_3H_7S \phantom{x} O\end{array}$ | 2 |
| $\begin{array}{c}C_2H_5O\\ \diagdown\\ \phantom{xx}P-SCH_2CH_2S(O)CH_3\\ \diagup \|\\ n\text{-}C_3H_7S \phantom{x} O\end{array}$ | 0 |
| $\begin{array}{c}C_2H_5O\\ \diagdown\\ \phantom{xx}P-SCH_2CHSCH_3\\ \diagup \| \phantom{xxx} \|\\ n\text{-}C_3H_7S \phantom{x} O \phantom{xx} CH_3\end{array}$ | 4 |

TABLE XV-continued
Field Control of Corn Earworm By O-Ethyl S'n-Propyl S-Alkylthioalkyl Dithiophosphates

| Experimental Compound (Applied at 1 lbs/acre) | Number of Infested Corn Ears (150 Ears Sampled) |
|---|---|
| None (Check) | 45 |

Example 28 — Control of Various Insects on Corn, Cabbage and Collards by O-Ethyl S'-n-Propyl-S-2-Methylthiopropyl Dithiophosphate

Test Procedures on Corn

Corn plots were planted on March 22. Each treatment was made on a 50 ft. row flanked by guard rows. Treatments were replicated 4 times and the average rating is reported. Except for insecticide treatment, the plots were managed in accordance with recommended farming practice for the area.

Corn earworm applications were made during silking on May 29, June 1, 2, 3, 4, 5, 8, 9, 10, 11 and 12. Readings were made on June 15.

Fall armyworm plots on sweet corn were treated on May 13, 20 and 27. Readings were made on May 29.

Test Procedures on Crucifers

King Cole cabbage and Vates Collards were transplanted on Feb. 1. Cabbage treatments were made on 50 ft. rows and replicated 4 times. Collard treatments were made on 25 ft. rows and replicated 4 times. Collard and cabbage rows were placed side-by-side and were flanked by guard rows. Except for insecticide treatment, the plots were managed in accordance with recommended farming practice for the area. Chemicals were applied on April 3, 10, 17, 24, May 1, 8, 15, 22 and 29, and readings were made on June 1.

Control of Insects

The pest control data are given in Table XVI. They show that the experimental dithiophosphate exhibits an excellent control of corn earworms at 0.5 lbs per acre application rate. The very difficult to control fall armyworm is well controlled on sweet by 0.75 lbs. per acre. Finally, the control of cabbage looper on cabbage and collards by 1.5 lbs. per acre is reflected in a sharply reduced damage when compared with the untreated checks.

TABLE XVI
Control of Corn Earworm, Fall Armyworm and Cabbage Looper by O-Ethyl S'-n-Propyl Dithiophosphate

| Dithiophosphate Rate (lbs./acre) | Corn Earworm, % Clean Ears | Fall Armyworm Injury Free Stalks of Sweet Corn, % | CabbageLooper Harvest Rating[1] | |
|---|---|---|---|---|
| | | | Cabbage | Collards |
| 0.5 | 94 | | | |
| Nil | 36 | | | |
| 0.75 | | 91 | | |
| Nil | | 67 | | |
| 1.5 | | | 3.8 | 2.0 |
| Nil | | | 5.9 | 5.3 |

[1]Higher ratings indicate more damage.

Additional Syntheses

The following examples 29–44 describe the preparation of those compounds tested in examples 14–28 which were not previously described.

Example 29. O,S-Diethyl S'-2-Ethylthiopropyl Dithiophosphate

O,O'-Diethyl S-1-(2-ethylthiopropyl)-dithiophosphate (11.6 g., 0.04 mole) and 4.5 g. (0.04 mole) of 1,4-diazabicyclo[2.2.2]octane, i.e., triethylenediamine, were stirred at ambient temperature for 24 hours. The resultant viscous liquid was dissolved in 100 ml. of acetonitrile and 8.7 g. (0.08 mole) of bromoethane were added. The solution was heated to 70° C. for 4 hours and cooled to ambient temperature. A white solid precipitated. This and the acetonitrile were dissolved in 50 ml. of water. The water phase then was separated and washed with 250 ml. of ether. The combined organic layers were washed with 50 ml. of 5% aqueous $NaHCO_3$, dried over anhydrous $MgSO_4$, and the solvent removed under vacuum under pressures down to 0.1 mm Hg. The liquid residue weighed 8.7 g. (87% pure gas liquid chromatography, i.e., glc.).

Analyses. Calculated for $C_9H_{21}O_2PS_3$: C, 37.47; H, 7.28; P, 10.77. Found: C, 37.28; H, 7.20; P, 10.56.

Example 30. O-Ethyl 1-Propyl S'-2-Ethylthioethyl Dithiophosphate

According to the procedure of Example 29, 27.4 g. (0.1 mole) of O,O'-diethyl S-1-(2-ethylthioethyl) dithiophosphate, 11.2 g. (0.1 mole) of triethylene diamine and 12.3 g. (0.1 mole) of 1-bromopropane were reacted to give 16.0 g. of a 79% pure product by glc.

Analyses. Calculated for $C_9H_{21}O_2PD_3$: C, 37.47; H, 7.28; P, 10.77; Found: C, 36.92; H, 7.27; P, 10.61.

Example 31. O-Ethyl S-1-Propyl S'-4-Chlorophenyllthiomethyl Dithiophosphate

According to the procedure of Example 29, 68.5 g. (0.2 mole) of O,O'-diethyl S-4-chlorophenylthiomethyl dithiophosphate, 22.4 g. (0.2 mole) triethylene diamine and 49.2 g. (0.4 mole) of 1-bromopropane were reacted to give 52 g. of a residual product whose structure was confirmed by nmr.

Analyses. Calculated for $C_{12}H_{18}ClO_2PS_3$: C, 40.41; H, 5.05; P, 8.69. Found: C, 40.23; H, 5.12; P, 8.49.

Example 32. O-Ethyl S-1-Propyl S'-2-Methylthiopropyl dithiophosphate

A quartz tube was charged with 48.0 g. (0.2 mole) of O-ethyl S-1-propyl S'-propenyl dithiophosphate and evacuated to 0.1 mm Hg. The tube was then cooled in a dry-ice-isopropanol bath and 18.1 g. (0.37 mole) of methanethiol were added. The tube was sealed and irradiated in a water bath with ultraviolet (UV) radiation from three 100 Watt Hanau immersion lamps at 15° from a distance of 6 cm. After 24 hours, the reaction was complete, as determined by gas chromatography (glc), and the excess methanethiol was removed under vacuum (0.1 mm). The residue was dissolved in 500 ml. of ether and washed with 50-ml. of 5% aqueous sodium bicarbonated. The ether solution was dried over anhydrous magnesium sulfate, and the solvent was removed under reduced pressure. The yield of O-ethyl S-1-propyl S'-1-(2-methylthiopropyl) dithiophosphate was 53.7 g. (85% pure by glc). The boiling point of the product was 127°-129° C. at 0.08 mm Hg.

Analyses. Calculated for $C_9H_{21}O_2PS_3$: C, 37.47; H, 7.28; P, 10.77. Found: C, 37.53; H, 7.28; P, 11.34.

Example 33. O-Ethyl S-1-Propyl S'-2-Ethylthiopropyl Dithiophosphate

This compound was prepared from 48.0 g. (0.2 mole) of O-ethyl S-1-propyl S'-propenyl dithiophosphate and 21.0 g. (0.33 mole) of ethanethiol under UV radiation according to the procedure of Example 32. The yield was 58.0 g. (82% pure by glc). The boiling point of product was 128°-129° C. at 0.17 mm Hg.

Analyses. Calculated for $C_{10}H_{23}O_2PS_3$: C, 39.76; H, 7.68; P, 10.27. Found: C, 39.91; H, 8.01; P, 9.73.

Example 34. O-Ethyl S-1-Propyl S'-2-n-Propylthiopropyl Dithiophosphate

This compound was prepared from 48.0 g. (0.2 mole) of O-ethyl S-1-propyl S'-propenyl dithiophosphate and 23.3 g. (0.3 mole) of i-propanethiol under UV radiation according to the procedure of Example 32. The yield was 55.0 g. The product decomposed upon distillation.

Analyses. Calculated for $C_{11}H_{25}O_2PS_3$: C, 41.77; H, 7.89; P, 9.81. Found: C, 41.96; H, 7.75; P, 9.47.

Example 35. O-Ethyl S-1-Propyl S'-2-i-Propylthiopropyl Dithiophosphate

O-Ethyl-S-1-propyl S'-propenyl dithiophosphate (24.0 g., 0.1 mole) and 11.4 g. (0.15 mole) 1-propanethiol were reacted according to the procedure of Example 32 to give 16.0 g. of product (50% yield).

Analyses. Calculated for $C_{11}H_{25}O_2PS_3$: C, 41.77; H, 7.89; P, 9.81. Found: C, 42.18; H, 7.84; P, 9.35.

Example 36. O-Ethyl S-1-Propyl S'-2-n-Hexylthiopropyl Dithiophosphate

O-Ethyl S-1-propyl S'-propenyl dithiophosphate (24.0 g., 0.1 mole) and 17.5 g. (0.15 mole) 1-hexanethiol were reached according to the procedure of Example 32 to give 34.7 g. of a residual product whose structure was confirmed by nmr.

Analyses. Calculated for $C_{14}H_{31}O_2PS_3$: C, 46.77; H, 9.14; P, 8.69. Found: C, 49.53; H, 8.66; P, 7.40.

Example 37. O-Ethyl S-2-Methylpropyl S'-2-Methylthiopropyl Dithiophosphate

This compound was prepared by reacting 5.08 g. (0.02 mole) of O-ethyl S-1-(2-methylpropyl) S'-propenyl dithiophosphate and excess methanethiol according to Example 32 to give 2.6 g. of a residual product, whose structure was confirmed by nmr.

Analyses. Calculated for $C_{10}H_{23}O_2PS_3$: C, 39.76; H, 7.68; P, 10.27. Found: C, 38.22; H, 6.95; P, 10.28.

Example 38. O-Ethyl S-1-Propyl S'-2-Methylthiobutyl Dithiophosphate

This compound was prepared by reacting 8.6 g. (0.034 mole) of O-ethyl S-1-propyl S'-1-butenyl dithiophosphate and excess methanethiol according to the procedure of Example 32 to give 5.6 g. of a residual product whose structure was confirmed by nmr.

Analyses. Calculated for $C_{10}H_{23}O_2PS_3$: C, 39.76; H, 7.68; P, 10.27. Found: C, 39.72; H, 7.60; P, 9.75.

Example 39. O-Ethyl S-1-Propyl S'-2-Methylthio-3,3-Dimethylbutyl Dithiophosphate This compound was prepared by reacting 6.9 g. (0.025 mole) of O-ethyl S-1-propyl S'-1-(3,3-dimethylbutenyl)dithiophosphate and excess methanethiol according to the procedure of Example 32 to give 4.3 g. of a liquid residual product whose structure was confirmed by nmr.

Analyses. Calculated for $C_{12}H_{27}O_2PS_3$: C, 43.90; H, 8.23; P, 9.45. Found: C, 44.79; H, 7.49; P, 7.25.

Example 40. O-Methyl S-1-Propyl S'-2-Methylthiopropyl Dithiophosphate

O-Methyl S-1-propyl S'-propenyl dithiophosphate (2.26 g., 0.01 mole) and excess methanethiol were reacted according to the procedure of Example 32 to give 2.0 g. of a residual product whose structure was confirmed by nmr.

Analyses. Calculated for $C_8H_{19}O_2PS_3$: C, 35.25; H, 6.94. Found: C, 31.15; H, 6.41.

Example 41. O-Ethyl S-1-Butyl S'-Methylthiopropyl Dithiophosphate

O-Ethyl S-1-butyl S'-propenyl dithiophosphate (7.62 g., 0.03 mole) and excess methanethiol were reacted according to the procedure of Example 32 to give 6.2 g. of a liquid residual product whose structure was confirmed by nmr.

Analyses. Calculated for $C_{10}H_{23}O_2PS_3$: C, 39.76; H, 7.68; P, 10.27. Found: C, 40.53; H, 7.58; P, 9.50.

Example 42. O-Ethyl S-2-Propyl S-2-Methylthiopropyl Dithiophosphate

O-Ethyl S-2-propyl S'-propenyl dithiophosphate (7.2 g., 0.03 mole) and excess methanethiol were reacted according to the procedure of Example 32 to give 6.0 g. of a residual product whose structure of compound was confirmed by nmr.

Analyses. Calculated for $C_9H_{21}O_2PS_3$: C, 37.47; H, 7.28. Found: C, 36.61; H, 7.03.

Example 43. O,S-Di-n-propyl S'-2-Methylthiopropyl dithiophosphate

O,S-Di-n-propyl S'-propenyl dithiophosphate (10.0 g, 0.039 mole) and excess methanethiol were reacted according to the procedure of Example 32 to give 10.1 g. of 84% pure product (72% yield).

Analyses. Calculated for $C_{10}H_{23}O_2PS_3$: C, 39.76; H, 7.68; P, 10.27. Found: C, 99; H, 7.75; P, 10.28.

Example 44. O-Ethyl S-n-Propyl S'-3-n-Propylthiopropyl Dithiophosphate

O-Ethyl S-n-propyl S'-allyldithiophosphate is reacted with a ten molar excess of n-propanethiol under the effect of UV at 15°. The progress of the reaction is estimated by nmr stectroscopy. After the reaction is substantially complete, the excess thiol is stripped in vacuo. The liquid residual product is mostly the desired dithiophosphate ester.

The conclusion, novel O-alkyl S'-alkyl S-hydrocarbylthioalkyl dithiophosphate compositions having unexpected, highly useful pesticidal properties were discovered. While the novel compositions are generally useful as animal and plant pesticides, it has been found that certain compositions are more attractive for economical use, lesser amounts of these compounds being sufficient for pest control. More specifically, O-ethyl S-n-propyl S'-hydrocarbylthioalkyl dithiophosphates represent a pesticidally very highly active but relatively non-toxic, novel class of pesticides. These pesticides are particularly attractive for the control of insects, mites, nematodes, foliar and soil fungi. Due to their high insecticidal effectiveness and low mammalian toxicity, they have a potentially high therapeutic index for application in animal health control.

We claim:

1. A pesticidal composition for combatting insects, nematodes, mites, and fungi comprising as an active ingredient, a pesticidally effective amount of a compound of the formula:

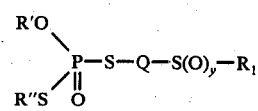

where R' is methyl or ethyl; R" is primary or secondary $C_3$ to $C_4$ alkyl; $R_1$ is $C_1$ to $C_3$ alkyl, phenyl or chlorophenyl; Q is $C_1$ to $C_4$ alkylene; and $y$ is 0 to 2; provided that when Q is methylene, $y$ is 0; and further comprising a carrier.

2. The pesticidal composition of claim 1, wherein R" is ethyl.

3. The pesticidal composition of claim 1, wherein R" is n-propyl.

4. The pesticidal composition of claim 1, wherein $y$ is 0.

5. The pesticidal composition of claim 1 wherein $R_1$ is $C_1$ to $C_4$ alkyl.

6. The pesticidal composition of claim 1 wherein Q is propylene.

7. A pesticidal composition according to claim 1 containing as an active ingredient the compound of the formula:

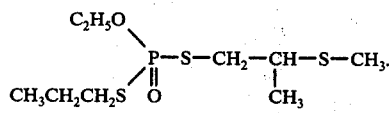

8. A pesticidal composition for combatting insects, nematodes, mites and fungi comprising as an active ingredient, a pesticidally effective amount of a compound of the formula:

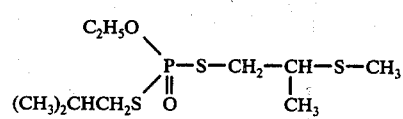

and a carrier.

9. A pesticidal composition for combatting insects, nematodes, mites and fungi comprising as an active ingredient a pesticidally effective amount of a compound of the formula:

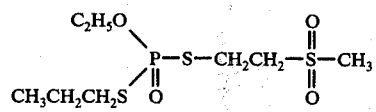

and a carrier.

10. A pesticidal composition for combatting insects, nematodes, mites and fungi comprising as an active ingredient a pesticidally effective amount of a compound of the formula:

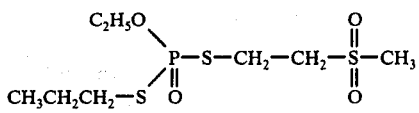

and a carrier.

11. A method for controlling pests which attack animals and plants, said pests selected from the group consisting of insects, nematodes, mites and fungi, comprising contacting said pests with a pesticidal amount of a compound of the formula

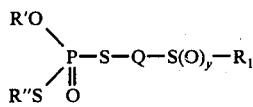

wherein R' is methyl or ethyl; R" is primary or secondary $C_3$ to $C_4$ alkyl; $R_1$ is $C_1$ to $C_3$ alkyl, phenyl or chlorophenyl; Q is $C_1$ to $C_4$ alkylene; and y is 0 to 2, provided that when Q is methylene, y is 0.

12. The method of claim 11 in which the compound is O-ethyl-S-n-propyl-S'-2-methylsulfinylethyl dithiophosphate, and the pests are insects.

13. The method of claim 11 in which the compound is O-ethyl-S-n-propyl-S'-2-methylsulfonylethyl dithiophosphate, and the pests are insects.

14. The method of claim 11 in which the compound is O-ethyl-S-isobutyl-S'-2-methylthiopropyl dithiophosphate, and the pests are insects.

15. The method of claim 11 in which the compound is O-ethyl-S-n-propyl-S'-2-methylthiophosphate, and the pests are insects.

16. A method for controlling insects which comprises contacting said insects with an insecticidal amount of a compound of the formula

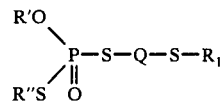

wherein R' is methyl or ethyl; R" is primary or secondary $C_3$ to $C_4$ alkyl; $R_1$ is $C_1$ to $C_3$ alkyl, phenyl or 4-chlorophenyl; and Q is $C_1$ to $C_3$ alkylene.

17. A method according to claim 16 in which R' is ethyl, R" is n-propyl, and $R_1$ is $C_1$ to $C_3$ alkyl.

18. The method of claim 16 in which the compound is O-ethyl-S-n-propyl-S'-2-ethylthioethyl dithiophosphate.

19. The method of claim 16 in which the compound is O-ethyl-S-n-propyl-S'-2-ethylthiopropyl dithiophosphate.

20. The method of claim 16 in which the compound is O-ethyl-S-n-propyl-S'-2-methylthioethyl dithiophosphate.

21. The method of claim 16 in which the compound is O-ethyl-S-n-propyl-S'-2-methylthiopropyl dithiophosphate.

22. the method of claim 16 in which the compound is O-ethyl-S-n-propyl-S'-2-n-propylthiopropyl dithiophosphate.

23. The method of claim 16 in which the compound is O-ethyl-S-n-propyl-S'-isopropylthioethyl dithiophosphate.

24. The method of claim 16 in which the compound is O-ethyl-S-n-propyl-S'-ethylthiomethyl dithiophosphate.

25. The method of claim 16 in which the compound is O-ethyl-S-n-propyl-S'-3-methylthiopropyl dithiophosphate.

26. The method of claim 16 in which the compound is O-ethyl-S-n-propyl-S'-2-isopropylthiopropyl dithiophosphate.

27. The method of claim 16 in which the compound is O-ethyl-S-n-propyl-S'-2-propylthioethyl dithiophosphate.

28. The method of claim 16 in which the compound is O-ethyl-S-n-propyl-S'-(4-chlorophenyl)-thiomethyl dithiophosphate.

* * * * *